United States Patent
Han

(10) Patent No.: US 9,984,306 B2
(45) Date of Patent: May 29, 2018

(54) METHOD AND APPARATUS FOR GENERATING A MEDICAL IMAGE, AND METHOD OF GENERATING PERSONALIZED PARAMETER VALUE

(71) Applicant: SAMSUNG ELECTRONICS CO., LTD., Suwon-si, Gyeonggi-do (KR)

(72) Inventor: Jeong-ho Han, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 321 days.

(21) Appl. No.: 14/298,192

(22) Filed: Jun. 6, 2014

(65) Prior Publication Data

US 2014/0363062 A1 Dec. 11, 2014

(30) Foreign Application Priority Data

Jun. 10, 2013 (KR) ........................ 10-2013-0066058

(51) Int. Cl.
- *G06K 9/00* (2006.01)
- *G06K 9/46* (2006.01)
- *G06F 19/00* (2018.01)
- *G06T 5/40* (2006.01)

(Continued)

(52) U.S. Cl.
CPC ............ *G06K 9/4642* (2013.01); *A61B 6/545* (2013.01); *G06F 19/321* (2013.01); *G06T 5/40* (2013.01); *G06T 5/50* (2013.01); *A61B 6/465* (2013.01); *A61B 6/467* (2013.01); *A61B 6/488* (2013.01); *A61B 6/5217* (2013.01); *A61B 6/542* (2013.01); *A61B 6/56* (2013.01); *G06T 2207/10116* (2013.01); *G06T 2207/20092* (2013.01); *G06T 2207/30004* (2013.01)

(58) Field of Classification Search
None
See application file for complete search history.

(56) References Cited

U.S. PATENT DOCUMENTS

| 6,768,784 B1 | 7/2004 | Green et al. |
| 2004/0136498 A1 | 7/2004 | Omernick et al. |

(Continued)

FOREIGN PATENT DOCUMENTS

| DE | 10 2008 014 738 | 9/2009 |
| EP | 1 004 984 | 11/1999 |

(Continued)

OTHER PUBLICATIONS

Extended European Search Report dated Oct. 31, 2014 in corresponding European Patent Application No. 14171594.

*Primary Examiner* — Weiwen Yang
(74) *Attorney, Agent, or Firm* — Staas & Halsey LLP

(57) ABSTRACT

A method of generating a personalized parameter value for generating a medical image includes acquiring a first medical image of an object, which is imaged according to a predetermined parameter value set in a medical imaging apparatus, and a second medical image changed from the first medical image, determining a first standard parameter value corresponding to the first medical image and a second standard parameter value corresponding to the second medical image, and generating a personalized parameter value corresponding to the object on the basis of the first standard parameter value and the second standard parameter value.

20 Claims, 19 Drawing Sheets

(51) Int. Cl.
　　　*G06T 5/50*　　　(2006.01)
　　　*A61B 6/00*　　　(2006.01)

(56) References Cited

U.S. PATENT DOCUMENTS

| | | | |
|---|---|---|---|
| 2005/0100201 A1* | 5/2005 | Mayer | G06F 19/3406 |
| | | | 382/128 |
| 2006/0193437 A1 | 8/2006 | Boeing et al. | |
| 2007/0140542 A1 | 6/2007 | Spahn | |
| 2007/0165930 A1* | 7/2007 | Feuerlein | G06T 1/60 |
| | | | 382/128 |
| 2009/0238329 A1 | 9/2009 | Haras | |
| 2009/0245603 A1* | 10/2009 | Koruga | A45D 44/00 |
| | | | 382/128 |
| 2009/0262892 A1 | 10/2009 | Haras | |
| 2011/0176710 A1* | 7/2011 | Mattiuzzi | G06F 19/321 |
| | | | 382/128 |
| 2012/0087474 A1 | 4/2012 | Foos et al. | |
| 2012/0201355 A1 | 8/2012 | Butzine et al. | |
| 2014/0270053 A1 | 9/2014 | Larson | |

FOREIGN PATENT DOCUMENTS

| | | |
|---|---|---|
| EP | 1 069 807 | 7/2000 |
| JP | 2005-270286 | 10/2005 |
| JP | 2005-296277 | 10/2005 |
| WO | WO 03/039371 | 5/2003 |
| WO | WO 2013/049818 | 4/2013 |

\* cited by examiner

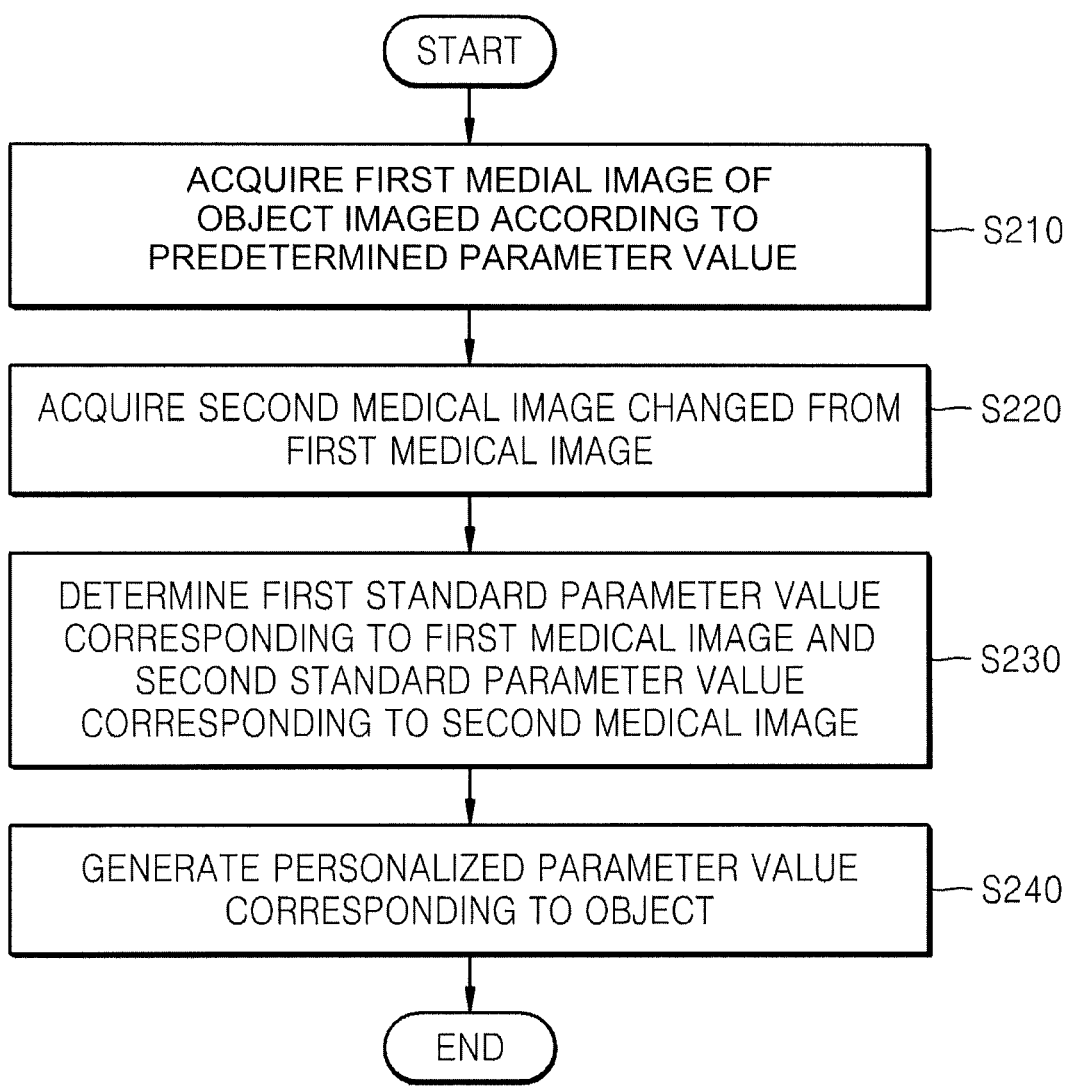

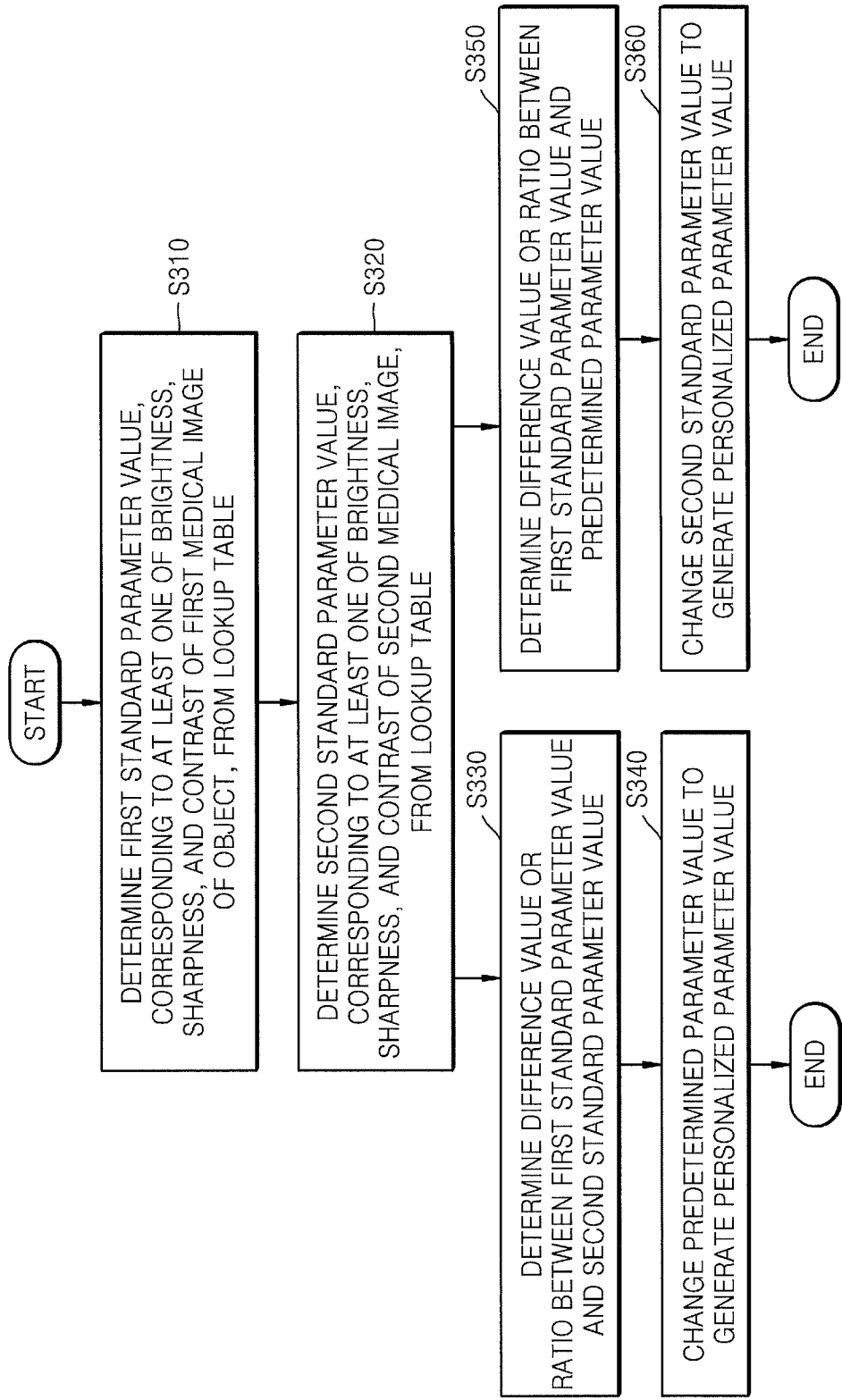

FIG. 5

| IMAGED PART (530) | BODY INFORMATION OF STANDARD OBJECT (550) | | | | CHARACTERISTIC OF STANDARD MEDICAL IMAGE (570) | | | STANDARD PARAMETER VALUE (510) | | |
|---|---|---|---|---|---|---|---|---|---|---|
| | SEX | AGE | WEIGHT (kg) | HEIGHT (cm) | BRIGHTNESS | SHARPNESS | CONTRAST | TUBE CURRENT (mA) | TUBE VOLTAGE (keV) | IRRADIATION TIME (SEC) |
| CHEST | MAN | 40~45 | 80~90 | 160~165 | 60 | 50 | 65 | 5 | 40 | 5 |
| CHEST | MAN | 45~50 | 70~80 | 170~175 | 40 | 40 | 45 | 4 | 50 | 4 |
| CHEST | WOMAN | 40~45 | 60~70 | 160~165 | 40 | 35 | 40 | 3 | 65 | 3 |
| HEAD | MAN | 30~35 | 60~70 | 170~175 | 50 | 55 | 60 | 6 | 40 | 4 |
| HEAD | WOMAN | 20~25 | 50~60 | 155~160 | 50 | 50 | 50 | 2 | 40 | 2 |
| HEAD | WOMAN | 10~15 | 20~30 | 120~125 | 40 | 40 | 55 | 1 | 35 | 2 |
| ... | ... | ... | ... | ... | ... | ... | ... | ... | ... | ... |

FIG. 6

| PREDETERMINED PARAMETER VALUE (610) | | | CHARACTERISTIC OF FIRST MEDICAL IMAGE (620) | | | FIRST STANDARD PARAMETER VALUE (630) | | |
|---|---|---|---|---|---|---|---|---|
| TUBE CURRENT (mA) | TUBE VOLTAGE (keV) | IRRADIATION TIME (SEC) | BRIGHTNESS | SHARPNESS | CONTRAST | TUBE CURRENT (mA) | TUBE VOLTAGE (keV) | IRRADIATION TIME (SEC) |
| 3.5 | 55 | 4 | 70 | 40 | 30 | 5 | 70 | 6 |

| PERSONALIZED PARAMETER VALUE (640) | | | CHARACTERISTIC OF SECOND MEDICAL IMAGE (650) | | | SECOND STANDARD PARAMETER VALUE (660) | | |
|---|---|---|---|---|---|---|---|---|
| TUBE CURRENT (mA) | TUBE VOLTAGE (keV) | IRRADIATION TIME (SEC) | BRIGHTNESS | SHARPNESS | CONTRAST | TUBE CURRENT (mA) | TUBE VOLTAGE (keV) | IRRADIATION TIME (SEC) |
| A | B | C | 50 | 50 | 40 | 4.5 | 55 | 5 |

FIG. 7

| IMAGED PART (720) | IDENTIFICATION INFORMATION OF OBJECT (730) | | BODY INFORMATION OF OBJECT (740) | | | | PRE-IMAGING INFORMATION (750) | | | | | | | | | PERSONALIZED PARAMETER VALUE (710) | | |
|---|---|---|---|---|---|---|---|---|---|---|---|---|---|---|---|---|---|---|
| | | | | | | | PRE-IMAGING PARAMETER VALUE | | | FIRST STANDARD PARAMETER VALUE | | | SECOND STANDARD PARAMETER VALUE | | | | | |
| | NAME | IMAGED DATE | AGE | SEX | WEIGHT (kg) | HEIGHT (cm) | TUBE CURRENT (mA) | TUBE VOLTAGE (keV) | IRRADIATION TIME (SEC) | TUBE CURRENT (mA) | TUBE VOLTAGE (keV) | IRRADIATION TIME (SEC) | TUBE CURRENT (mA) | TUBE VOLTAGE (keV) | IRRADIATION TIME (SEC) | TUBE CURRENT (mA) | TUBE VOLTAGE (keV) | IRRADIATION TIME (SEC) |
| CHEST | HONG KILDONG | 2013.04.10 | 33 | MAN | 67 | 176 | 7 | 80 | 5 | 11 | 95 | 6 | 8 | 70 | 6 | A | B | C |

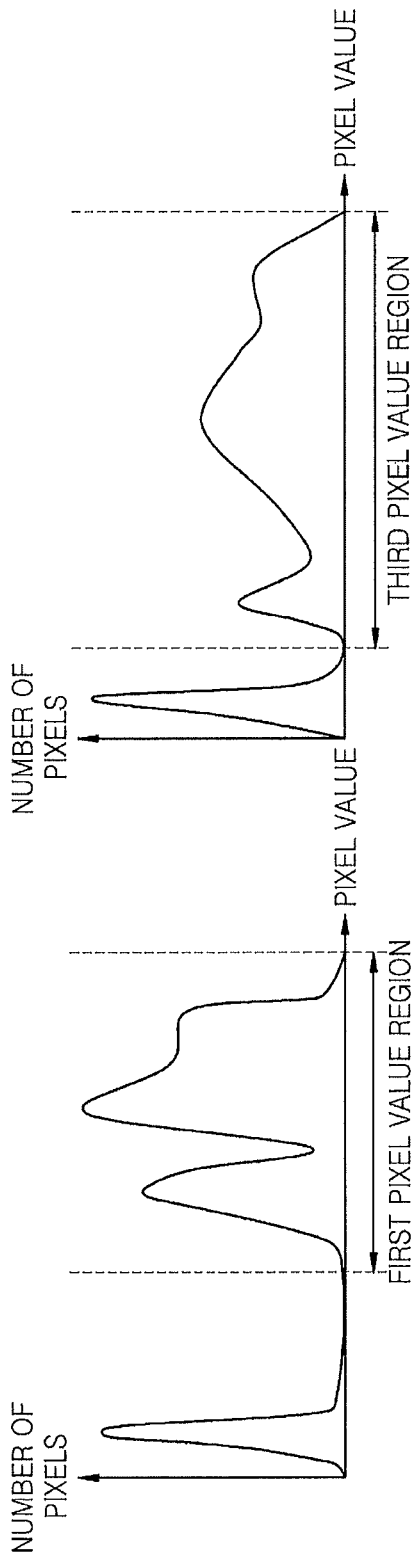
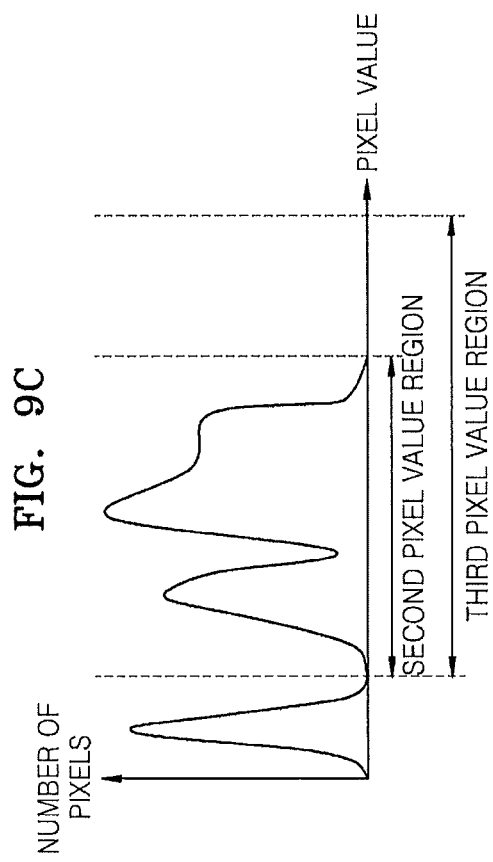

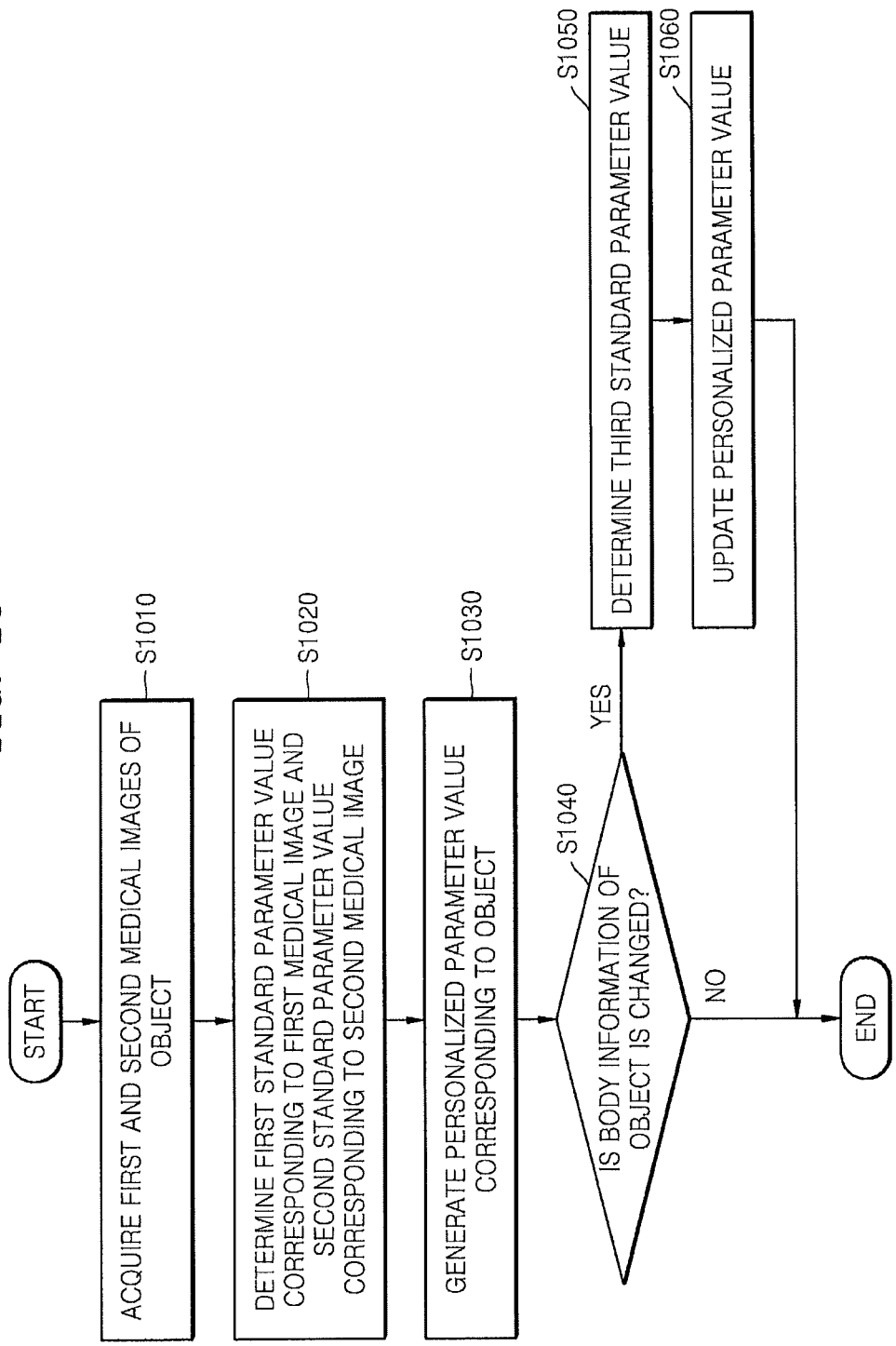

FIG. 11

| PREDETERMINED PARAMETER VALUE (1110) | | | CHARACTERISTIC OF FIRST MEDICAL IMAGE (1120) | | | FIRST STANDARD PARAMETER VALUE (1130) | | |
|---|---|---|---|---|---|---|---|---|
| TUBE CURRENT (mA) | TUBE VOLTAGE (keV) | IRRADIATION TIME (SEC) | BRIGHTNESS | SHARPNESS | CONTRAST | TUBE CURRENT (mA) | TUBE VOLTAGE (keV) | IRRADIATION TIME (SEC) |
| 3.5 | 55 | 4 | 70 | 40 | 30 | 5 | 70 | 6 |
| PERSONALIZED PARAMETER VALUE (1140) | | | CHARACTERISTIC OF SECOND MEDICAL IMAGE (1150) | | | SECOND STANDARD PARAMETER VALUE (1160) | | |
| TUBE CURRENT (mA) | TUBE VOLTAGE (keV) | IRRADIATION TIME (SEC) | BRIGHTNESS | SHARPNESS | CONTRAST | TUBE CURRENT (mA) | TUBE VOLTAGE (keV) | IRRADIATION TIME (SEC) |
| A | B | C | 50 | 50 | 40 | 4.5 | 55 | 5 |
| UPDATED PERSONALIZED PARAMETER VALUE (1170) | | | CHARACTERISTIC OF SECOND MEDICAL IMAGE (1180) | | | THIRD STANDARD PARAMETER VALUE (1190) | | |
| TUBE CURRENT (mA) | TUBE VOLTAGE (keV) | IRRADIATION TIME (SEC) | BRIGHTNESS | SHARPNESS | CONTRAST | TUBE CURRENT (mA) | TUBE VOLTAGE (keV) | IRRADIATION TIME (SEC) |
| D | E | F | 50 | 50 | 40 | 5 | 65 | 6 |

METHOD AND APPARATUS FOR GENERATING A MEDICAL IMAGE, AND METHOD OF GENERATING PERSONALIZED PARAMETER VALUE

CROSS-REFERENCE TO RELATED APPLICATIONS

This application claims the benefit of Korean Patent Application No. 10-2013-0066058, filed on Jun. 10, 2013, in the Korean Intellectual Property Office, the disclosure of which is incorporated herein in its entirety by reference.

BACKGROUND

1. Field

One or more embodiments relate to a method and apparatus for generating a medical image and a method of generating a personalized parameter value, and more particularly, to a method and apparatus for generating a medical image and a method of generating a personalized parameter value, which generate or provide optimal parameter values for each object in order to control an amount of radiation irradiated on an object.

2. Description of the Related Art

X-ray image imaging apparatuses are equipment that observe an internal structure of an organic body by using X-rays. Examples of the X-ray imaging apparatuses include X-ray apparatuses, computed tomography (CT) apparatuses, position emission tomography (PET) apparatuses, etc.

Since the X-ray imaging apparatuses irradiate X-rays on a human body, the human body is exposed to the X-rays. A human body is exposed to X-rays of about 2 to 10 mSv, depending on the method used when imaging an X-ray image. Such an exposure amount corresponds to the amount of X-rays that a human body is exposed to in everyday life over a period of about eight months to three years. However, in pregnant women, exposure to X-rays can cause a critical disease and complications to a fetus, and critically influence the growth and development of the fetus. For this reason, a method that decreases an amount of X-rays to which a human body is exposed to when being observed by the X-ray imaging apparatuses is needed.

SUMMARY

One or more embodiments relate to an apparatus and method for generating a medical image and a method of generating a personalized parameter value, which control an amount of X-rays exposed to an object by using the parameter value optimized for the object.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

The foregoing described problems may be overcome and/or other aspects may be achieved by one or more embodiments of a method of generating a personalized parameter value. The method may include acquiring a first medical image of an object, which may be imaged according to a predetermined parameter value set in a medical imaging apparatus, and a second medical image changed from the first medical image; determining a first standard parameter value corresponding to the first medical image and a second standard parameter value corresponding to the second medical image; and generating a personalized parameter value corresponding to the object on a basis of the first standard parameter value and the second standard parameter value.

The medical imaging apparatus may include, for example, an X-ray apparatus, a CT apparatus, and the like.

The second medical image may include a medical image which may be generated by changing an image characteristic of the first medical image.

The determining of a first standard parameter value and a second standard parameter value may include determining the first standard parameter value corresponding to the first medical image and the second standard parameter value corresponding to the second medical image from a lookup table.

The image characteristic of each of the first and second medical images may include at least one of a brightness, sharpness, and contrast of a medical image.

The determining of a first standard parameter value and a second standard parameter value may include determining the first standard parameter value and the second standard parameter value which correspond to body information and an imaged part of the object.

The body information of the object may include at least one of an age, sex, weight, and height of the object.

The lookup table may include a plurality of standard parameter values, the plurality of standard parameter values respectively corresponding to body information and imaged part of each of a plurality of standard objects.

The lookup table may include a plurality of standard parameter values, the plurality of standard parameter values respectively corresponding to image characteristic of each of a plurality of medical images.

When the second medical image includes a medical image which is generated by changing a contrast of the first medical image, and there is no second standard parameter value corresponding to a contrast of the second medical image, the determining of a second standard parameter value may include determining the contrast of the second medical image as the contrast of the first medical image to determine the second standard parameter value corresponding to the second medical image.

The determining of a second standard parameter value may include: determining a second pixel value region, having a total sum of pixel values which is less than a total sum of pixel values in a first pixel value region on a histogram of the first medical image, on a histogram of the second medical image; and determining the second standard parameter value corresponding to a brightness of the second medical image when the pixels included in the first pixel value region are moved to the second pixel value region.

The determining of the second standard parameter value may include: determining a third pixel value region on the histogram of the second medical image, wherein the third pixel value region comprises pixel values corresponding to a number of pixels that is changed from a number of pixels corresponding to pixel values of the histogram of the first medical image; and determining, as the second pixel value region, a region from a start point of the third pixel value region to a point separated therefrom by a distance of the first pixel value region.

The generating of a personalized parameter value may include changing the predetermined parameter value according to a relationship between the first standard parameter value and the second standard parameter value to generate the personalized parameter value.

The generating of a personalized parameter value may include changing the second standard parameter value according to a relationship between the first standard parameter value and the predetermined parameter value to generate the personalized parameter value.

The method may further include: when body information of the object is changed after the personalized parameter value is generated, determining a third standard parameter value, corresponding to an image characteristic of the second medical image and the changed body information of the object, from a lookup table; and updating the personalized parameter value on the basis of the third standard parameter value.

The parameter value set in the medical imaging apparatus may include, for example, at least one of a tube current, a tube voltage, and an X-ray irradiation time, etc.

The method may further include outputting the personalized parameter value.

The method may further include mapping the personalized parameter value to identification information and body information of the object to store the mapped parameter value.

The method may further include mapping the personalized parameter value to an imaged part of the object to store the mapped parameter value.

The foregoing described problems may be overcome and/or other aspects may be achieved by one or more embodiments of a medical imaging method of generating a medical image of an object. The method may include receiving identification information of the object from a user; outputting a personalized parameter value corresponding to the identification information of the object; receiving a selection of the personalized parameter value from the user; and generating the medical image of the object according to the selection of the personalized parameter value.

The outputting of a personalized parameter value may include displaying a second medical image changed from a pre-imaged first medical image of the object according to the personalized parameter value and a predetermined parameter value set in a medical imaging apparatus.

The displaying may include displaying an adjustment window for adjusting the personalized parameter value.

When the user changes the personalized parameter value by using the adjustment window, the displaying may include changing the second medical image according to the changed personalized parameter value, and displaying the changed second medical image as a medical image to be imaged.

The medical imaging method may further include: determining a first standard parameter value and a second standard parameter value which respectively correspond to a pre-imaged first medical image of the object and a second medical image changed from the first medical image according to the predetermined parameter value set in the medical imaging apparatus; and generating the personalized parameter value on the basis of the first standard parameter value and the second standard parameter value.

The receiving of identification information may include receiving body information of the object, and the medical imaging method may further include: when the body information of the object inputted by the user differs from body information of the object of when the first medical image is photographed, determining a third standard parameter value corresponding to the second medical image and the body information of the object inputted by the user; and updating the personalized parameter value corresponding to the identification information of the object.

The medical imaging method may further include outputting the updated personalized parameter value.

The foregoing described problems may be overcome and/or other aspects may be achieved by one or more embodiments of a medical imaging apparatus. The apparatus may include a medical image acquirer to acquire a first medical image of an object, which is imaged according to a predetermined parameter value set in a medical imaging apparatus, and a second medical image changed from the first medical image; a determiner to determine a first standard parameter value corresponding to the first medical image and a second standard parameter value corresponding to the second medical image; and a generator to generate a personalized parameter value corresponding to the object on a basis of the first standard parameter value and the second standard parameter value.

The medical imaging apparatus may include, for example, an X-ray apparatus, a CT apparatus, etc.

The second medical image may include a medical image which may be generated by changing an image characteristic of the first medical image.

The determiner may determine the first standard parameter value corresponding to the first medical image and the second standard parameter value corresponding to the second medical image from a lookup table.

The image characteristic of each of the first and second medical images may include, for example, at least one of a brightness, sharpness, and contrast, etc. of a medical image.

The determiner may determine the first standard parameter value and the second standard parameter value which correspond to body information and an imaged part of the object.

The body information of the object may include, for example, at least one of an age, sex, weight, and height of the object, etc.

The lookup table may include a plurality of standard parameter values, the plurality of standard parameter values respectively corresponding to body information and imaged parts of a plurality of standard objects.

The lookup table may include a plurality of standard parameter values, the plurality of standard parameter values respectively corresponding to image characteristics of a plurality of medical images.

When the second medical image includes a medical image which is generated by changing a contrast of the first medical image, and there is no second standard parameter value corresponding to a contrast of the second medical image, the determiner may determine the contrast of the second medical image as the contrast of the first medical image to determine the second standard parameter value corresponding to the second medical image.

The determiner may determine a second pixel value region, having a total sum of pixel values which is less than a total sum of pixel values in a first pixel value region on a histogram of the first medical image, on a histogram of the second medical image, and determine the second standard parameter value corresponding to a brightness of the second medical image when the pixels included in the first pixel value region are moved to the second pixel value region.

The determiner may determine a third pixel value region, whose number of pixels is changed in comparison with the histogram of the first medical image, on the histogram of the second medical image, and determine a region from a start point of the third pixel value region to a point separated therefrom by a distance of the first pixel value region as the second pixel value region.

The generator may change the predetermined parameter value according to a relationship between the first standard parameter value and the second standard parameter value to generate the personalized parameter value.

The generator may change the second standard parameter value according to a relationship between the first standard parameter value and the predetermined parameter value to generate the personalized parameter value.

When body information of the object is changed after the personalized parameter value is generated, the determiner may determine a third standard parameter value, corresponding to an image characteristic of the second medical image and the changed body information of the object, from a lookup table, and the generator may update the personalized parameter value on the basis of the third standard parameter value.

The parameter value set in the medical imaging apparatus may include, for example, at least one of a tube current, a tube voltage, and an X-ray irradiation time, etc.

The medical imaging apparatus may further include an output to output the personalized parameter value.

The medical imaging apparatus may further include a storage to map the personalized parameter value to identification information and body information of the object to store the mapped parameter value.

The medical imaging apparatus may map the personalized parameter value to an imaged part of the object to store the mapped parameter value.

The foregoing described problems may be overcome and/or other aspects may be achieved by one or more embodiments of a medical imaging apparatus for generating a medical image of an object The apparatus may include a user input to receive identification information of the object from a user; an output to output a personalized parameter value corresponding to the identification information of the object; and a imager to receive a selection of the personalized parameter value from the user through the user input unit, and images the medical image of the object according to the selection of the personalized parameter value.

The output may include a display to display a second medical image changed from a pre-imaged first medical image of the object according to the personalized parameter value and a predetermined parameter value set in a medical imaging apparatus.

The display may display an adjustment window for adjusting the personalized parameter value.

When the user changes the personalized parameter value by using the adjustment window, the display may change the second medical image according to the changed personalized parameter value, and display the changed second medical image as a medical image to be imaged.

The medical imaging apparatus may further include a determiner to determine a first standard parameter value and a second standard parameter value which respectively correspond to a pre-imaged first medical image of the object and a second medical image changed from the first medical image according to the predetermined parameter value set in the medical imaging apparatus; and a generator to generate the personalized parameter value on the basis of the first standard parameter value and the second standard parameter value.

The user input may receive body information of the object. When the body information of the object inputted by the user differs from body information of the object of when the first medical image is imaged, the determiner may determine a third standard parameter value corresponding to the second medical image and the body information of the object inputted by the user. The generator may update the personalized parameter value corresponding to the identification information of the object.

The output may output the updated personalized parameter value.

The foregoing described problems may be overcome and/or other aspects may be achieved by one or more embodiments of a non-transitory computer-readable storage medium storing a computer program for executing the method of generating a personalized parameter value.

The foregoing described problems may be overcome and/or other aspects may be achieved by one or more embodiments of a non-transitory computer-readable storage medium storing a computer program for executing the medical imaging method.

BRIEF DESCRIPTION OF THE DRAWINGS

These and/or other aspects will become apparent and more readily appreciated from the following description of embodiments, taken in conjunction with the accompanying drawings of which:

FIG. 2 is a flowchart illustrating a method of generating a personalized parameter value according to one or more embodiments;

FIG. 3 is a flowchart illustrating a method of generating a personalized parameter value according to one or more embodiments;

FIG. 5 is a diagram showing a lookup table including standard parameter values according to one or more embodiments;

FIG. 6 is a diagram for describing a method of generating a personalized parameter value according to one or more embodiments;

FIG. 7 is a diagram illustrating object-imaging information including a personalized parameter value generated by the method of generating a personalized parameter value according to one or more embodiments;

FIG. 9A is a histogram of the first medical image illustrated in FIG. 8A;

FIG. 9B is a histogram of the second medical image illustrated in FIG. 8B;

FIG. 9C is a histogram modified from the histogram of FIG. 9B according to one or more embodiments;

FIG. 10 is a flowchart illustrating a method of updating a personalized parameter value according to one or more embodiments;

FIG. 11 is a diagram for describing the method of updating a personalized parameter value according to one or more embodiments;

DETAILED DESCRIPTION

Figure 1:
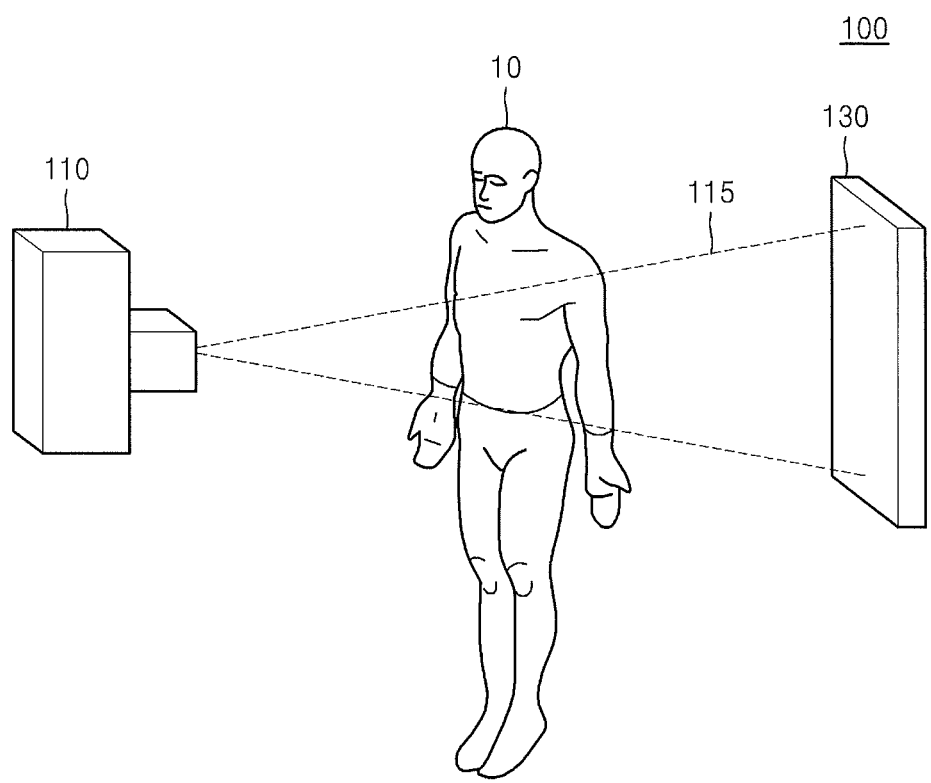
FIG. 1 is a diagram illustrating a state in which X-rays emitted from a medical imaging apparatus according to one or more embodiments pass through an object.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

Terms used herein will be briefly described, and the present invention will be described in detail.

Terms used in the present invention have been selected as general terms which are widely used at present, in consideration of the functions of the present invention, but may be altered according to the intent of an operator skilled in the art, conventional practice, or introduction of new technology. Also, if there is a term which is arbitrarily selected by the applicant in a specific case, in which case a meaning of the term will be described in detail in a corresponding description portion of the specification. Therefore, the terms should be defined on the basis of the entire content of this specification instead of a simple name of each of the terms.

In this disclosure below, when it is described that one comprises (or includes or has) some elements, it should be understood that it may comprise (or include or has) only those elements, or it may comprise (or include or have) other elements as well as those elements if there is no specific limitation. The term "module", as used herein, may mean, but is not limited to, a software or hardware component, such as a Field Programmable Gate Array (FPGA) or an Application Specific Integrated Circuit (ASIC), which performs certain tasks. A module may advantageously be configured to reside in the addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

The term "image" used herein may denote multi-dimensional data composed of discrete image factors (for example, pixels in a two-dimensional (2D) image and pixels in a three-dimensional (3D) image). For example, an image may include a medical image of an object which is acquired by an X-ray apparatus, a CT apparatus, a magnetic resonance imaging (MRI) apparatus, an ultrasonic apparatus, or another medical imaging apparatus.

Moreover, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume very close to a density of organisms and an effective atomic number, and may include a spherical phantom having a temper similar to a human body.

Moreover, the "user" used herein is a medical expert, and may be a doctor, a nurse, a medical technologist, a medical image expert, or the like, or may be an engineer repairing a medical apparatus. However, the user is not limited thereto.

FIG. 1 is a diagram illustrating a state in which X-rays emitted from a medical imaging apparatus 100 according to one or more embodiments pass through an object.

The medical imaging apparatus 100 according to one or more embodiments may include an X-ray generator 110 that may emit X-rays 115 toward an object 10 and a detector 130 that may detect the X-rays 115 passing through the object 10. The medical imaging apparatus 100 may acquire a medical image of the object 10 by using the X-rays 115 that may be detected by the detector 130. The medical imaging apparatus 100 according to one or more embodiments may include an imaging apparatus, which may acquire a medical image of the object 10 by using the X-rays 115, such as, for example, an X-ray apparatus, a CT apparatus, a PET apparatus, or the like.

Referring to FIG. 1, the X-ray generator 110 of the medical imaging apparatus 100 may directly emit the X-rays 115 toward the object 10, and thus, the object 10 may be exposed to the X-rays 115. An amount of X-rays irradiated on the object 10 may be determined with parameter values set in the medical imaging apparatus 100, and the parameter values may include, for example, a tube current value, a tube voltage value, and an X-ray irradiation time, etc.

Despite using the same parameter value to image the object 10, an image quality of medical images generated may vary depending on body information of the object 10. The reason is because a transmittance of the X-rays 115 is changed depending on a density and thickness of fat, muscle, bone, or the like.

Therefore, a general user may image the object 10 with a high parameter value to acquire a medical image whose a quality may be ensured at a certain level. However, if the object 10 transmits X-rays better than an average object, then the object 10 may be exposed to an excessive amount of X-rays due to a parameter value set by a user. On the other hand, if the object 10 does not transmit X-rays better than the average object, then a poor-quality medical image may be acquired due to the parameter value set by the user, and for this reason, the user must re-image the object 10, possibly causing the object 10 to be exposed to excessive X-rays.

Moreover, the image quality of medical images acquired based on a parameter value which is arbitrarily set by a user with no consideration of body information may not be constant, and thus, the user may perform post-correction that may change a characteristic of a medical image. That is, when a medical image of the object 10 is excessively bright or is very low in contrast, the user may perform post-correction that may lower a brightness of the medical image or may enhance a contrast of the medical image, thereby possibly enhancing a readability of the medical image.

An image quality of the post-corrected medical image may also be an image quality of a medical image desired by the user, and thus, when the image quality of a medical image acquired from the object 10 is the same as the image quality of the post-corrected medical image, the object 10 may avoid being exposed to an unnecessary amount of X-rays.

The medical imaging apparatus 100 according to an embodiment of the present invention may generate the parameter value optimized or personalized for the object 10 by using the medical image acquired from the object 10 and the post-corrected medical image.

FIG. 2 is a flowchart illustrating a method of generating a personalized parameter value according to one or more embodiments.

In operation S210, the medical imaging apparatus 100 may acquire a first medical image of the object 10 imaged based on a predetermined parameter value. The predetermined parameter value may be previously set by a user.

In operation S220, the medical imaging apparatus 100 may acquire a second medical image changed from the first medical image.

The second medical image is a medical image which may be generated by post-correcting the first medical image. The second medical image may be generated by changing a characteristic of the first medical image. A characteristic of a medical image may include, for example, at least one of a brightness, a chroma, a color, a sharpness, and a contrast, etc. That is, the second medical image may include a medical image which has been generated by changing, for example, at least one of a brightness, chroma, color, sharpness, and contrast, etc. of the first medical image.

In operation S230, the medical imaging apparatus 100 may determine a first standard parameter value corresponding to the first medical image and a second standard parameter value corresponding to the second medical image.

The standard parameter value may be previously determined based on body information of a standard object, an imaged part of the standard object, and a characteristic of a standard medical image, and stored in the medical imaging apparatus 100. The standard parameter value may be stored as a lookup table in the medical imaging apparatus 100.

Specifically, the medical imaging apparatus 100 may determine a first standard parameter value corresponding to a characteristic of the first medical image from the lookup table, and determine a second standard parameter value corresponding to a characteristic of the second medical image from the lookup table.

Moreover, the medical imaging apparatus 100 may determine the first standard parameter value and the second standard parameter value in further consideration of body information and an imaged part of the object 10. A method that determines the first standard parameter value and the second standard parameter value by using the lookup table will be described below with reference to FIGS. 4 and 5.

In operation S240, the medical imaging apparatus 100 may generate a personalized parameter value corresponding to the object 10 on the basis of the first standard parameter value and the second standard parameter value.

The medical imaging apparatus 100 may change a predetermined parameter value set in the medical imaging apparatus 100 according to a relationship between the first standard parameter value and the second standard parameter value to generate a personalized parameter value, and may also change the second standard parameter value according to the relationship between the first standard parameter value and the predetermined parameter value to generate the personalized parameter value. This will be described below with reference to FIG. 6.

The personalized parameter value generated by one or more embodiments may denote the parameter value optimized for the object 10, for acquiring a medical image having the same quality as that of the second medical image.

When imaging the object 10 by using the personalized parameter value, a quality of the medical image acquired from the object 10 may match a quality of a medical image desired by the user. As a result, the medical imaging apparatus 100 according to one or more embodiments may prevent unnecessary X-rays from being irradiated on the object 10 due to an unnecessarily high parameter value being arbitrarily set by the user, and may prevent the object 10 from having to be re-imaged due to a low parameter value is set by the user.

FIG. 3 is a flowchart illustrating a method of generating a personalized parameter value according to one or more embodiments.

In operation S310, the medical imaging apparatus 100 may determine a first standard parameter value, corresponding to, for example, at least one of a brightness, sharpness, and contrast, etc. of a first medical image of the object 10 imaged based on a predetermined parameter value, from a lookup table.

In operation S320, the medical imaging apparatus 100 may determine a second standard parameter value, corresponding to, for example, at least one of a brightness, sharpness, and contrast, etc. of a second medical image which is generated by changing at least one of, for example, the brightness, sharpness, and contrast, etc. of the first medical image, from the lookup table.

The medical imaging apparatus 100 may analyze the first medical image and the second medical image to determine, for example, the brightness, sharpness, and contrast, etc. of each of the first and second medical images. For example, the medical imaging apparatus 100 may determine a numerical value corresponding to, for example, each of the brightness, sharpness, and contrast, etc. of each of the first medical image and the second medical image in consideration of pixel values of the first and second medical images, a distribution of the pixels values, and a pixel value difference between a specific pixel and a pixel adjacent thereto. For example, the medical imaging apparatus 100 may determine a brightness of each of the first and second medical images by using an average value or median value of the pixel values of pixels included in the first and second medical image. Also, the medical imaging apparatus 100 may determine, for example, a brightness, sharpness, and contrast, etc. of all regions included in the first and second medical images, and may also determine, for example, a brightness, sharpness, and contrast, etc. of select regions or a region of interest (ROI) included in the first and second medical images. Here, the select regions or the ROI may be previously set by a user.

In operation S330, the medical imaging apparatus 100 may determine a difference value or a ratio between the first standard parameter value and the second standard parameter value.

When each of the first standard parameter value and the second standard parameter value includes a tube current value, the medical imaging apparatus 100 may determine a difference value or a ratio between the tube current value of the first standard parameter value and the tube current value of the second standard parameter value.

In operation S340, the medical imaging apparatus 100 may change a predetermined parameter value set in the medical imaging apparatus 100 to generate a personalized parameter value. For example, the medical imaging apparatus 100 may apply the difference value or ratio between the tube current value of the first standard parameter value and the tube current value of the second standard parameter value to a tube current value of the predetermined parameter value, thereby acquiring a tube current value of the personalized parameter value.

In parallel to operations S330 and S340, in operation S350, the medical imaging apparatus 100 may determine a difference value or a ratio between the first standard parameter value and the predetermined parameter value.

When each of the first standard parameter value and the second standard parameter value includes the tube current value, the medical imaging apparatus 100 may determine the difference value or ratio between the tube current value of the first standard parameter value and the tube current value of the second standard parameter value.

In operation S360, the medical imaging apparatus 100 may change the second standard parameter value to generate a personalized parameter value. For example, the medical imaging apparatus 100 may apply a difference value or a ratio between the tube current value of the first standard parameter value and the tube current value of the predetermined parameter value to the tube current value of the second standard parameter value, thereby possibly acquiring a tube current value of the personalized parameter value.

Hereinafter, an exemplary method that determines the first standard parameter value corresponding to the first medical image and the second standard parameter value corresponding to the second medical image will be described below with reference to FIGS. 4A, 4B and 5.

Figure 4A:
FIG. 4A is a diagram illustrating a first medical image of an object.
Figure 4B:
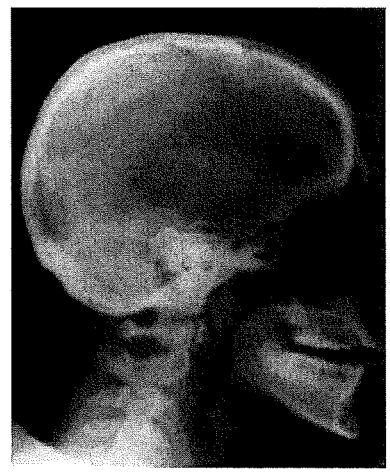
FIG. 4B is a diagram illustrating a second medical image that is generated by changing the first medical image.

FIG. 4A is a diagram illustrating the first medical image of the object 10, and FIG. 4B is a diagram illustrating the second medical image that is generated by changing the first medical image.

For purposes of illustration, it may be assumed that a user imaged the object 10 with a predetermined parameter value to acquire the first medical image of FIG. 4A, and post-processed the first medical image to acquire the second medical image of FIG. 4B.

FIG. 5 is a diagram showing a lookup table including standard parameter values according to one or more embodiments.

The lookup table may include an imaged part 530 and body information 550 of a standard object, a characteristic 570 of a standard medical image, and a plurality of standard parameter values 510 corresponding thereto. The characteristic 570 of the standard medical image as illustrated in FIG. 5 includes only a brightness, a sharpness, and a contrast, but it is obvious to those skilled in the art that the characteristic 570 of the standard medical image may further include, for example, a chroma, color, etc. of the standard medical image.

As an example, the first row of the lookup table denotes that a standard medical image having a brightness of 60, a sharpness of 50, and a contrast of 65 is acquired when a chest of a standard male having an age of 40 to 45, a weight of 80 to 90 kg, and a height of 160 to 165 cm is imaged and parameter values such as a tube current value of 5 mA, a tube voltage value of 40 keV, and an irradiation time of 5 sec are used. Also, as an example, the third row of the lookup table denotes that a standard medical image having a brightness of 40, a sharpness of 35, and a contrast of 40 is acquired when a chest of a standard female having an age of 40 to 45, a weight of 60 to 70 kg, and a height of 160 to 165 cm is imaged and parameter values such as a tube current value of 3 mA, a tube voltage value of 65 keV, and an irradiation time of 3 sec are used.

Data of the lookup table may be acquired by using a statistical value of information acquired from a plurality of objects.

Referring again of FIGS. 4A and 4B, the medical imaging apparatus 100 may map the brightness, sharpness, and contrast of the first medical image and body information and an imaged part of an object to the lookup table of FIG. 5 to determine the first standard parameter value, and may map the brightness, sharpness, and contrast of the second medical image and the body information and imaged part of the object to the lookup table to determine the second standard parameter value. When the lookup table of FIG. 5 further includes, for example, a color and a chroma as the characteristic 570 of the standard medical image, the medical imaging apparatus 100 may determine the first standard parameter value and the second standard parameter value in further consideration of, for example, a color and chroma of the first medical image and a color and chroma of the second medical image.

Subsequently, the medical imaging apparatus 100 may determine a personalized parameter value corresponding to the object 10 by using the first standard parameter value, the second standard parameter value, and the predetermined parameter value set in the medical imaging apparatus 100.

FIG. 6 is a diagram for describing a method of generating a personalized parameter value according to one or more embodiments.

Referring to FIG. 6, a predetermined parameter value 610 set in the medical imaging apparatus 100 may include a tube current value of 3.5 mA, a tube voltage value of 55 keV, and an irradiation time of 4 sec, and a first standard parameter value 630 may include a tube current value of 5 mA, a tube voltage value of 70 keV, and an irradiation time of 6 sec. That is, the tube current value and irradiation time of the predetermined parameter value 610 may be lower than those of the first standard parameter value 630, respectively.

Generally, when a tube current value and an irradiation time are high, a brightness of a medical image is enhanced, but a brightness of a first medical image (which is acquired with the predetermined parameter value 610 including a low tube current value and a low irradiation time) being the same as a brightness of a medical image acquired with the first standard parameter value 630 may denote that the object 10 transmits X-rays better than the standard object.

For purposes of illustration, it may be assumed that a user imaged the object 10 with the predetermined parameter value 610 while expecting to acquire a medical image having the same characteristic as a characteristic 650 of a second medical image, but the first medical image actually acquired was brighter than the second medical image. Accordingly, it may be seen that unnecessary X-rays may have been irradiated on the object 10.

The medical imaging apparatus 100 according to one or more embodiments may change a second standard parameter value 660 to generate a personalized parameter value 640 according to a relationship between the predetermined parameter value 610 and the first standard parameter value 630. For example, there is a difference of 1.5 mA between a tube current value of 3.5 mA of the predetermined parameter value 610 and a tube current value of 5 mA of the first standard parameter value 630, and thus, the medical imaging apparatus 100 may subtract a current value of 1.5 mA from a tube current value of 4.5 mA of the second standard parameter value 660, thereby determining a tube current value A of the personalized parameter value 640. Alternatively, the medical imaging apparatus 100 may determine a ratio between the tube current value of 3.5 mA of the predetermined parameter value 610 and the tube current value of 5 mA of the first standard parameter value 630, and may apply the determined ratio to the tube current value of 4.5 mA of the second standard parameter value 660 to determine the tube current value A of the personalized parameter value 640.

Moreover, the medical imaging apparatus 100 according to one or more embodiments may change the predetermined parameter value 610 to generate the personalized parameter value 640 according to a relationship between the first standard parameter value 630 and the second standard parameter value 660. For example, there is a difference of 0.5 mA between a tube current value of 5 mA of the first standard parameter value 630 and the tube current value of 4.5 mA of the second standard parameter value 660, and thus, the medical imaging apparatus 100 may subtract a current value of 0.5 mA from the tube current value of 3.5 mA of the predetermined parameter value 610, thereby determining the tube current value A of the personalized parameter value 640. Alternatively, the medical imaging apparatus 100 may determine a ratio between the tube current value of 5 mA of the first standard parameter value 630 and the tube current value of 4.5 mA of the second standard parameter value 660, and may apply the determined ratio to the tube current value of 3.5 mA of the predetermined parameter value 610 to determine the tube current value A of the personalized parameter value 640.

FIG. 7 is a diagram illustrating object-imaging information including a personalized parameter value 710 generated by a method of generating a personalized parameter value according to one or more embodiments. The medical imaging apparatus 100 may store the personalized parameter value 710 corresponding to the object 10 along with at least one of an imaged part 720, identification information 730, body information 740, and pre-imaging information 750 of the object 10. When object-imaging information is generated and then a chest of the object 10 having a name "Hong Kildong" is re-imaged, the medical imaging apparatus 100 according to one or more embodiments may image the object 10 by using the personalized parameter value 710 of FIG. 7, thus possibly decreasing an amount of X-rays irradiated on the object 10.

Generally, a tube current value and an irradiation time among the parameter values of the medical imaging apparatus 100 affect a brightness of an image, and a tube voltage value affects a sharpness of the image depending on the Compton effect, but the tube current value, the irradiation time, and the tube voltage value do not substantially affect a contrast of the image. Therefore, a problem may occur when the second standard parameter value mapped to a contrast of the second medical image changed from the first medical image is not in the lookup table.

Therefore, the following description will be made of a method that may determine the second standard parameter value when the second standard parameter value mapped to the contrast of the second medical image is not in the lookup table.

Figure 8A:
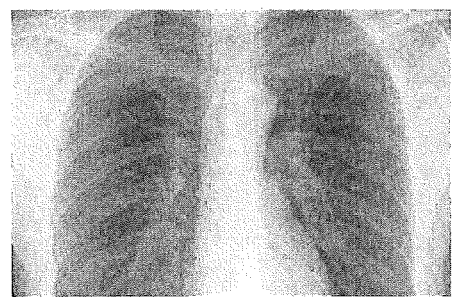
FIG. 8A is a diagram illustrating a first medical image of an object.
Figure 8B:
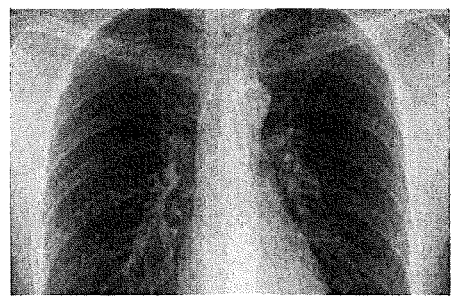
FIG. 8B is a diagram illustrating a second medical image that is generated by changing a contrast of the first medical image.

FIG. 8A is a diagram illustrating the first medical image of the object 10, and FIG. 8B is a diagram illustrating the second medical image that is generated by changing the contrast of the first medical image.

The changing of the contrast denotes that a contrast between a relatively bright portion and a relatively dark portion becomes clear.

FIG. 9A is a histogram of the first medical image illustrated in FIG. 8A, FIG. 9B is a histogram of the second medical image illustrated in FIG. 8B, and FIG. 9C is a histogram modified from the histogram of FIG. 9B according to one or more embodiments.

In FIGS. 9A to 9C, the abscissa axis indicates pixel values, and the ordinate axis indicates the number of pixels. The higher the pixel value, the brighter the pixel.

Referring to FIG. 9A, it can be seen that pixels included in the first medical image of FIG. 8A predominantly have a high pixel value.

Referring to FIG. 9B, it can be seen that the number of pixels having a relatively low pixel value increases in the second medical image of FIG. 8B compared to the first medical image. That is, the number of pixels corresponding to a dark region increases, and thus, a contrast of an image is enhanced.

It can be seen that pixels corresponding to a first pixel value region of FIG. 9A are spread on the histogram and then included in a third pixel value region of FIG. 9B. That is, the user changed pixel values of pixels having the pixel value of the first pixel value region in the first medical image, thereby changing the contrast of the first medical image.

A characteristic of the second medical image, for example, a brightness, sharpness, and contrast of the second medical image, may be determined for determining the second standard parameter value corresponding to the second medical image. Here, the sharpness of the second medical image may be determined as sharpness of the second medical image itself, and thus, a method of determining the brightness and contrast of the second medical image will be described below.

First, the contrast of the second medical image may be determined as the contrast of the first medical image. When the contrast of the second medical image is determined as the contrast of the first medical image, a shape of the histogram of FIG. 9B may become the same as that of the histogram of FIG. 9A. That is, the characteristic of the first medical image may become the same as that of the second medical image.

As described above, since a general user may tend to set a high parameter value for imaging the object 10, as the second standard parameter value may become lower, a personalized parameter value may become lower, and thus, an amount of X-rays irradiated on the object 10 may be reduced.

Therefore, in order to determine the brightness of the second medical image, the pixels included in the first pixel value region of FIG. 9A may be moved to a second pixel value region included in the third pixel value region, and then the brightness of the second medical image may be determined by using the pixels moved to the second pixel value region.

FIG. 9C shows the histogram in which the pixels included in the first pixel value region of FIG. 9A are moved to the second pixel value region included in the third pixel value region. A region whose total sum of pixel values is less than the total sum of the pixel values of the first pixel value region may be determined as the second pixel value region. Also, a region from a start point of the third pixel value region to a point separated therefrom by a distance of the first pixel value region may be determined as the second pixel value region, and thus, the brightness of the second medical image may be reduced.

As a result, when the second standard parameter value, which is mapped to the contrast of the second medical image which is generated by changing the contrast of the first medical image, is not in the lookup table, the contrast of the second medical image may be determined as the contrast of the first medical image, the brightness of the second medical image may be determined by using the pixels moved to the second pixel value region on the histogram of the second medical image, and then the second standard parameter value corresponding to the determined contrast and brightness may be determined. However, when the object 10 is imaged using the personalized parameter value generated by the above-described method, a medical image having a contrast desired by the user is not acquired, and thus, the user may perform a post-process that enhances a contrast of an acquired medical image.

FIG. 10 is a flowchart illustrating a method of updating a personalized parameter value according to one or more embodiments.

In operation S1010, the medical imaging apparatus 100 may acquire the first and second medical images of the object 10. The second medical image may include a medical image which is generated by changing a characteristic of the first medical image.

In operation S1020, the medical imaging apparatus 100 may determine the first standard parameter value corresponding to the first medical image and the second standard parameter value corresponding to the second medical image.

A standard parameter value may be previously determined based on body information and an imaged part of a standard object and a characteristic of a standard medical image, and stored in the corresponding to the first medical image. The standard parameter value may be stored as a lookup table in the medical imaging apparatus 100.

Specifically, the medical imaging apparatus 100 may determine the first standard parameter value, corresponding to, for example, at least one of the brightness, sharpness, and contrast, etc. of the first medical image, from the lookup table, and may determine the second standard parameter value, corresponding to, for example, at least one of the brightness, sharpness, and contrast, etc. of the second medical image, from the lookup table.

In operation S1030, the medical imaging apparatus 100 may generate the personalized parameter value corresponding to the object 10 by using the first standard parameter value and the second standard parameter value.

The medical imaging apparatus 100 may change the predetermined parameter value set in the medical imaging apparatus 100 according to the relationship between the first standard parameter value and the second standard parameter value to generate the personalized parameter value, and may also change the second standard parameter value according to the relationship between the first standard parameter value and the predetermined standard parameter value to generate the personalized parameter value.

In operation S1040, the medical imaging apparatus 100 may generate the personalized parameter value, and then may determine whether the body information of the object 10 is changed.

The body information of the object 10 may include, for example, at least one of an age, weight, height, an amount of body fat, and an amount of muscle, etc. of the object 10. Whether the body information of the object 10 is changed may be determined based on whether at least one of, for example, the age, weight, height, an amount of body fat, and an amount of muscle, etc. of the object 10 increases to be above or decreases to be below a predetermined threshold value.

In operation S1050, when the body information of the object 10 is determined as being changed, the medical imaging apparatus 100 may determine a third standard parameter value corresponding to the body information of the object 10.

As described above, in the lookup table including the standard parameter values, a plurality of the standard parameter values may respectively correspond to the body information and imaged part of the standard object and the characteristic of the standard medical image. Therefore, the medical imaging apparatus 100 may determine the third standard parameter values corresponding to the body information of the object 10 and the characteristic of the second medical image from the lookup table.

In operation S1060, therefore, the medical imaging apparatus 100 may update the personalized parameter value corresponding to the object 10 on the basis of the third standard parameter value.

The personalized parameter value, which was determined by using the first standard parameter value and the second standard parameter value which were determined before the body information of the object 10 was changed, may not be not optimized for the object 10 whose the body information was changed, and thus, the personalized parameter value may be updated in operation S1060 based on current body information of the object 10.

A method, which updates the personalized parameter value corresponding to the object 10 by using the third standard parameter value according to one or more embodiments, will be described with reference to FIG. 11.

FIG. 11 is a diagram for describing the method of updating a personalized parameter value according to one or more embodiments.

Referring to FIG. 11, a predetermined parameter value 1110 set in the medical imaging apparatus 100 may include, for example, a tube current value of 3.5 mA, a tube voltage value of 55 keV, and an irradiation time of 4 sec, and a first standard parameter value 1130 may include, for example, a tube current value of 5 mA, a tube voltage value of 70 keV, and an irradiation time of 6 sec. Also, a second standard parameter value 1160 may include, for example, a tube current value of 4.5 mA, a tube voltage value of 55 keV, and an irradiation time of 5 sec, and a third standard parameter value 1160 may include, for example, a tube current value of 5 mA, a tube voltage value of 65 keV, and an irradiation time of 6 sec. The personalized parameter value 1140 may be previously generated by changing the predetermined parameter value 1130 according to a relationship between the first standard parameter value 1130 and the second standard parameter value 1160, or may be previously generated by changing the second standard parameter value 1160 according to a relationship between the first standard parameter value 1130 and the predetermined parameter value 1110. However, since the personalized parameter value 1140 may be generated before the body information of the object 10, the personalized parameter value 1140 may be updated for the object 10 whose current body information is changed.

The medical imaging apparatus 100 according to one or more embodiments may generate an updated personalized parameter value 1170 by changing the third standard parameter value 1190, according to a relationship between the personalized parameter value 1140 and the second standard parameter value 1160. For example, there is a difference of "A−4.5 mA" between a tube current value A of the personalized parameter value 1140 and a tube current value of 4.5 mA of the second standard parameter value 1160, and thus, the medical imaging apparatus 100 may determine a tube current value D of the updated personalized parameter value 1170 by adding "A−4.5 mA" to a tube current value of 5 mA of the third standard parameter value 1190. Alternatively, the medical imaging apparatus 100 may determine a ratio between the tube current value A of the personalized parameter value 1140 and the tube current value of 4.5 mA of the second standard parameter value 1160, and may apply the determined ratio to the tube current value of 5 mA of the third standard parameter value 1190 to determine the tube current value D of the updated personalized parameter value 1170.

Moreover, the medical imaging apparatus 100 according to one or more embodiments may change the personalized parameter value 1140 to generate the updated personalized parameter value 1170 according to a relationship between the second standard parameter value 1160 and the third standard parameter value 1190. For example, there is a difference of 0.5 mA between the tube current value of 4.5 mA of the second standard parameter value 1160 and the tube current value of 5 mA of the third standard parameter value 1190, and thus, the medical imaging apparatus 100 may add a current value of 0.5 mA to the tube current value A of the personalized parameter value 1140, thereby determining the tube current value D of the updated personalized parameter value 1170. Alternatively, the medical imaging apparatus 100 may determine a ratio between the tube current value of 4.5 mA of the second standard parameter value 1160 and the tube current value of 5 mA of the third standard parameter value 1190, and may apply the determined ratio to the tube current value A of the personalized parameter value 1140 to determine the tube current value D of the updated personalized parameter value 1170.

Moreover, the medical imaging apparatus 100 according to one or more embodiments may generate the updated personalized parameter value 1170 by changing the third standard parameter value 1190, according to a relationship between the predetermined parameter value 1110 and the first standard parameter value 1130.

Moreover, the medical imaging apparatus 100 according to one or more embodiments may generate the updated personalized parameter value 1170 by changing the predetermined parameter value 1110, according to a relationship between the first standard parameter value 1130 and the third standard parameter value 1190.

Figure 12:
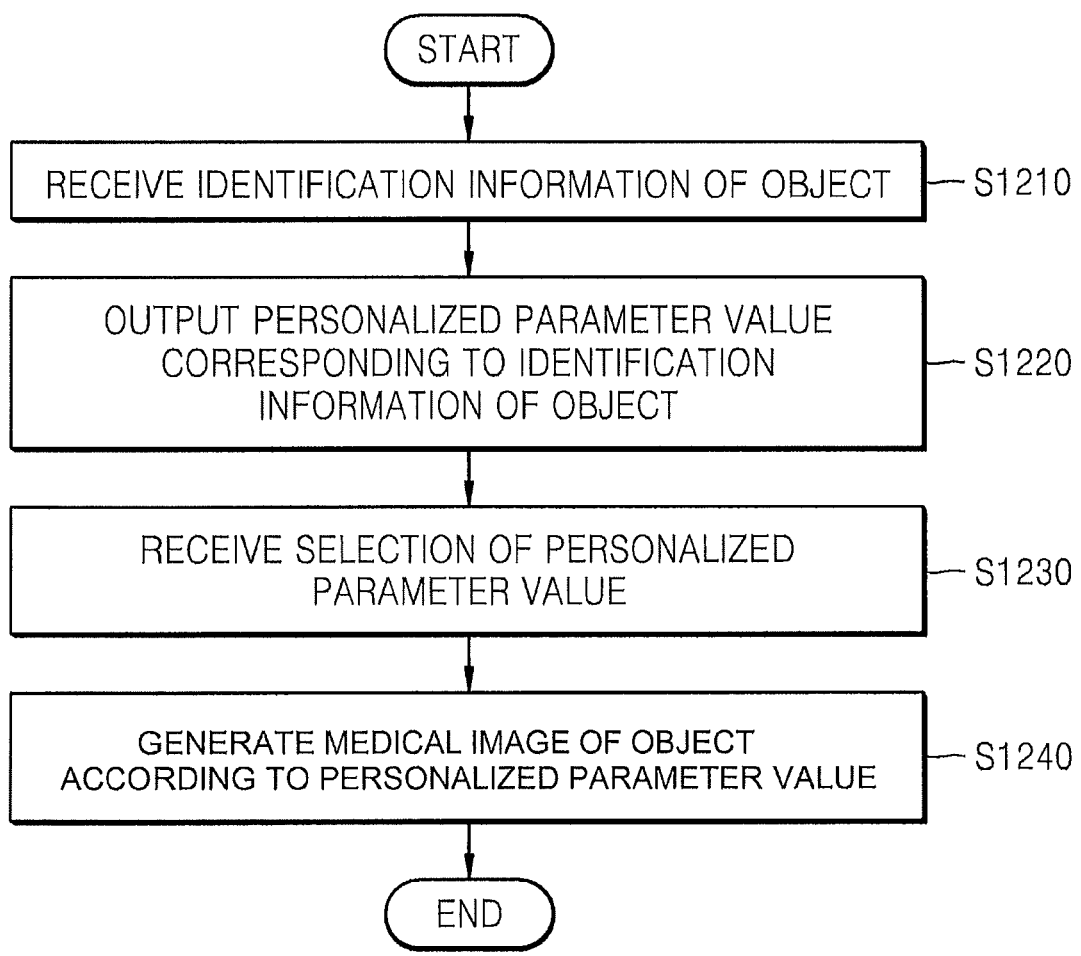
FIG. 12 is a flowchart illustrating a medical imaging method according to one or more embodiments.

FIG. 12 is a flowchart illustrating a medical imaging method according to one or more embodiments.

In operation S1210, the medical imaging apparatus 100 may receive identification information of the object 10. A user may input the identification information of the object 10 into the medical imaging apparatus 100 by using an input device such as a mouse, a keyboard, or the like, or the medical imaging apparatus 100 may receive the identification information of the object 100 from an external server.

In operation S1220, the medical imaging apparatus 100 may output a personalized parameter value corresponding to the identification information of the object 10.

As described above with reference to FIG. 7, the medical imaging apparatus 100 may map the personalized parameter value corresponding to the identification information of the object 10 to the body information and imaged part of the object 10 to store the personalized parameter value as object-imaging information. The medical imaging apparatus 100 may acquire the object-imaging information corresponding to the identification information of the object 10 inputted from the user, and may output the personalized parameter value included in the object-imaging information.

In operation S1230, the medical imaging apparatus 100 may receive selection of a personalized parameter value from the user.

In operation S1240, the medical imaging apparatus 100 may generate a medical image of the object 10 according to the personalized parameter value selected by the user.

Figure 13:
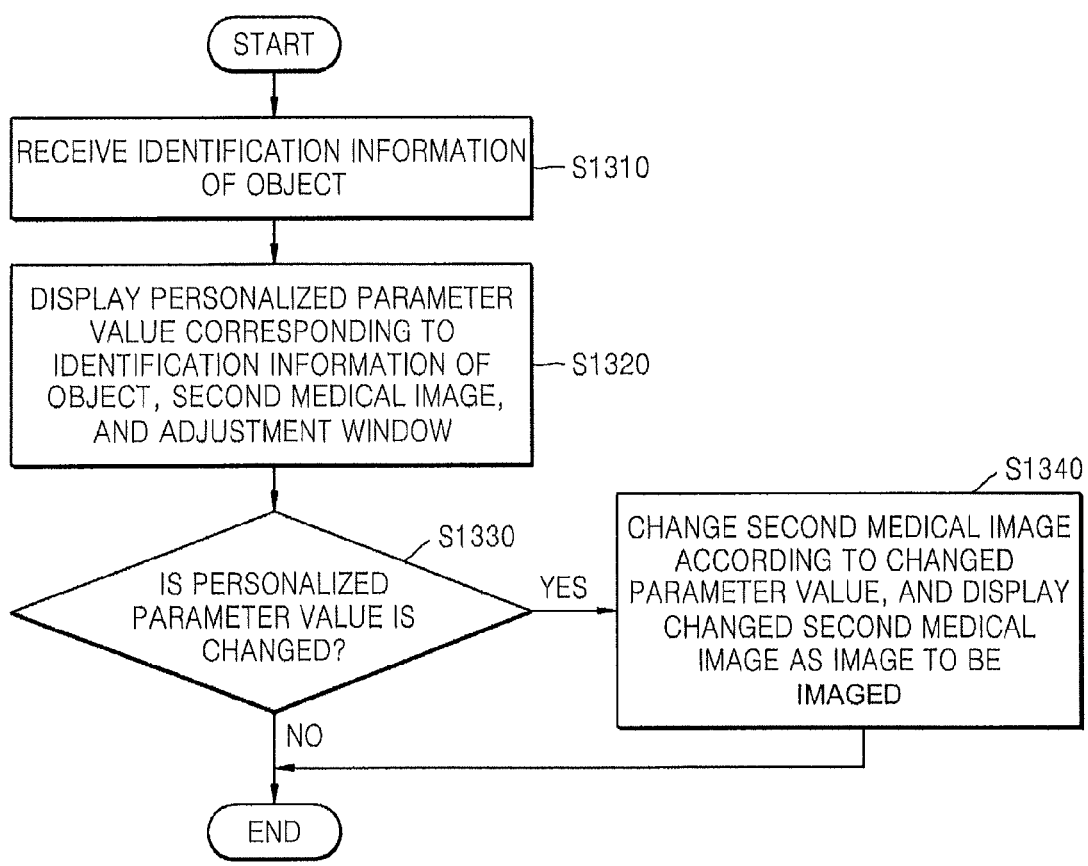
FIG. 13 is a flowchart illustrating a medical imaging method according to one or more embodiments.

FIG. 13 is a flowchart illustrating a medical imaging method according to one or more embodiments. FIG. 13 illustrates a method of changing a personalized parameter value according to one or more embodiments.

In operation S1310, the medical imaging apparatus 100 may receive the identification information of the object 10.

In operation S1320, the medical imaging apparatus 100 may display a personalized parameter value corresponding to the identification information of the object 10, the second medical image, and an adjustment window.

The second medical image may be a medical image which is generated by changing the characteristic of the first medical image. The reason that the medical imaging apparatus 100 displays the second medical image is so that the user may preview an image (which will be acquired according to the personalized parameter value) when the object 10 is imaged according to the personalized parameter value, and thus a medical image having the same quality as that of the second medical image may be acquired. The adjustment window may include a user interface for changing the personalized parameter value.

In operation S1330, the medical imaging apparatus 100 may determine whether the personalized parameter value is changed through the adjustment window.

In operation S1340, when the personalized parameter value is changed, the medical imaging apparatus 100 may change the second medical image according to the changed parameter value, and may display the changed medical image as an image to be imaged.

When the user changes at least one parameter value of, for example, a tube current value, tube voltage value, and irradiation time, etc. of the personalized parameter value by using the adjustment window, the medical imaging apparatus 100 may determine a standard parameter value mapped to the changed parameter value from the lookup table. Subsequently, the medical imaging apparatus 100 may change and output the second medical image according to a characteristic of the standard medical image corresponding to the determined standard parameter value.

Therefore, the user may previously check a medical image to be acquired and a quality thereof according to a parameter value set by the user.

Figure 14:
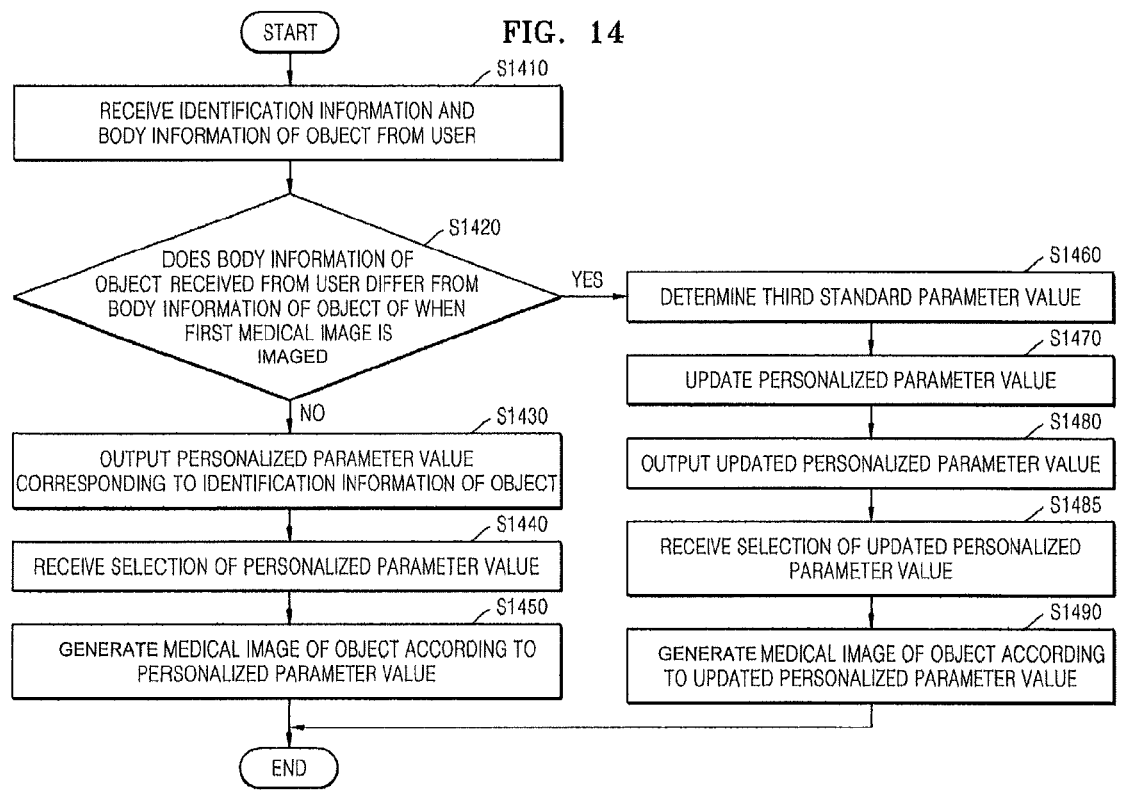
FIG. 14 is a flowchart illustrating a medical imaging method according to one or more embodiments.

FIG. 14 is a flowchart illustrating a medical imaging method according to one or more embodiments. FIG. 14 illustrates a method of updating a personalized parameter value according to one or more embodiments.

In operation S1410, the medical imaging apparatus 100 may receive the identification information and body information of the object 10 from a user.

In operation S1420, the medical imaging apparatus 100 may determine whether the body information of the object 10 received from the user differs from the body information of the object 10 that was obtained when the first medical image was imaged. The first medical image includes a pre-imaged medical image of the object 10.

In operation S1430, when the body information of the object 10 received from the user does not differ from the body information of the object 10 that was obtained when the first medical image was imaged, the medical imaging apparatus 100 may output a personalized parameter value corresponding to the identification information of the object 10.

In operation S1440, the medical imaging apparatus 100 may receive a selection of a personalized parameter value from the user.

In operation S1450, the medical imaging apparatus 100 may generate a medical image of the object 10 according to the personalized parameter value selected by the user.

When it is determined in operation S1420 that the body information of the object 10 received from the user differs from the body information of the object 10 of when the first medical image is imaged, the medical imaging apparatus 100 may determine a third standard parameter value corresponding to the body information of the object 10 inputted from the user in operation S1460. The third standard parameter value may include a standard parameter value corresponding to the body information of the object 10 and the characteristic of the second medical image.

In operation S1470, the medical imaging apparatus 100 may update the personalized parameter value corresponding to the object 10 according to the third standard parameter value. A method of updating the personalized parameter value has been described above, and thus, its detailed description is not provided.

In operation S1480, the medical imaging apparatus 100 may output the updated personalized parameter value.

In operation S1485, the medical imaging apparatus 100 may receive selection of the updated personalized parameter value.

In operation S1490, the medical imaging apparatus 100 may generate a medical image of the object 10 according to the updated personalized parameter value.

Figure 15:
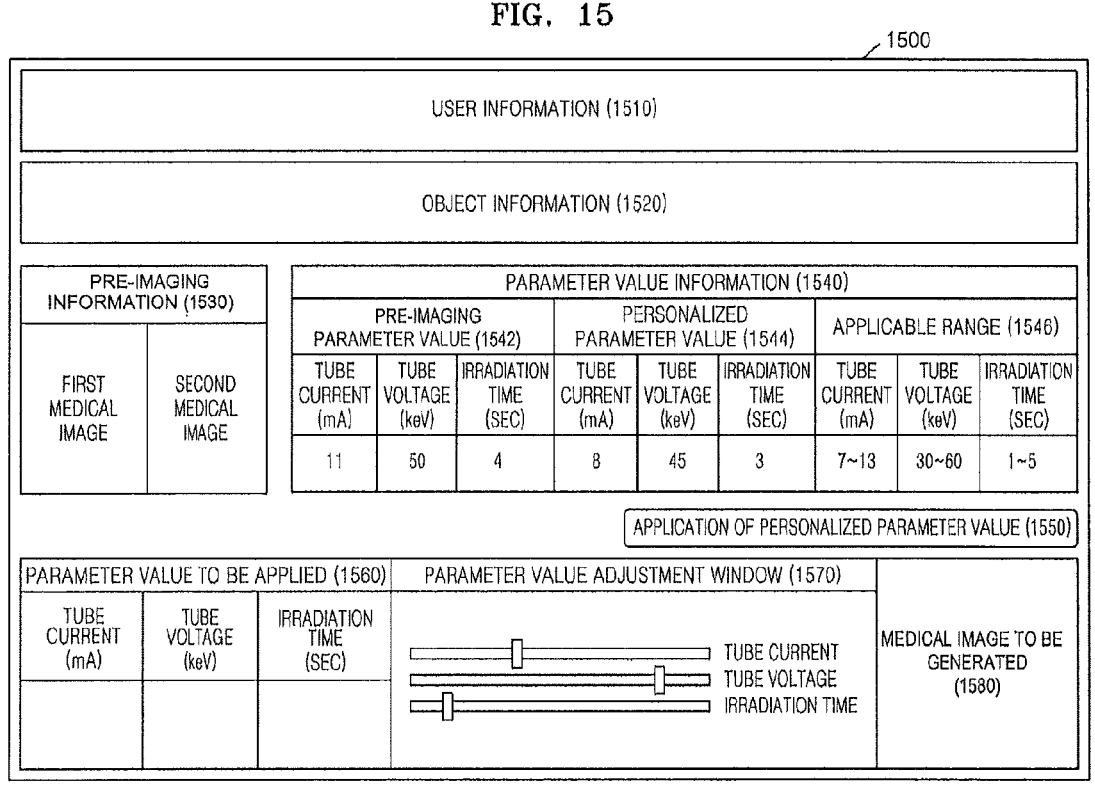
FIG. 15 is a diagram illustrating a screen outputted by a display of the medical imaging apparatus according to one or more embodiments.

FIG. 15 is a diagram illustrating a screen output by a display 1500 of the medical imaging apparatus 100 according to one or more embodiments.

Referring to FIG. 15, a screen outputted by the display 1500 may include user information 1510, object information 1520, pre-imaging information 1530, parameter value information 1540, a personalized parameter value application button 1550, a parameter value 1560 to be applied, a parameter value adjustment window 1570, and a medical image 1580 to be generated.

Identification information such as a name, an age, etc. of a user generating a medical image of the object 10 may be displayed in the user information 1510.

The identification information such as the name, etc. of the object 10 that will be imaged by the medical image, body information including a weight, a height, etc. of the object 10, and an imaged date and imaged part of the object 10 may be displayed in the object information 1520.

The pre-imaged first medical image of the object 10 and the second medical image changed from the first medical image may be displayed in the pre-imaging information 1530.

The parameter value information 1540 may include a pre-imaging parameter value 1542, a personalized parameter value 1544, and an applicable range 1546.

The pre-imaging parameter value 1542 may denote a parameter value which is set for imaging the first medical image, and the personalized parameter value 1544 may denote a parameter value which is generated on the basis of the pre-imaging parameter value 1542. Also, the applicable range 1546 may denote a range of parameter values that may be set in the medical imaging apparatus 100 according to the imaged part of the object 10 and a imaging mode. That is, referring to FIG. 15, a tube current value of 7 to 13 mA, a tube voltage value of 30 to 60 keV, and an irradiation time of 1 to 5 sec, may be set for imaging a current object 10. The user may determine whether to change the personalized parameter value 1544 on the basis of the applicable range 1546.

The personalized parameter value application button 1550 may select whether to image the object 10 by using the personalized parameter value 1544 generated by the medical imaging apparatus 100. The user may select the personalized parameter value application button 1550 by using, for example, a mouse, a keyboard, a trackball, or a touch screen, etc. and perform a setting in order for the object 10 to be imaged according to the personalized parameter value 1544.

The parameter value 1560 to be applied may denote a parameter value which is set in the medical imaging apparatus 100 for imaging the object 10. When the user selects the personalized parameter value application button 1550, the parameter value 1560 to be applied may denote the personalized parameter value 1544.

The parameter value adjustment window 1570 may present user interface for adjusting a parameter value displayed in the parameter value 1560 to be applied. The user may laterally move a slider displayed on a bar corresponding to each of, for example, a tube current, a tube voltage, and an irradiation time, etc. thereby adjusting, for example, a tube current value, tube voltage value, and irradiation time, etc. of the parameter value 1560 to be applied. The parameter value adjustment window 1570 of FIG. 15 is merely an example, and other user interface embodiments may be employed. For example, the user may directly input a numerical value.

The medical image 1580 to be imaged may denote a medical image of the object 10 able to be acquired according to the parameter value 1560 to be applied. As described above, when the user changes parameter value 1560 to be applied by using the parameter value adjustment window 1570, a characteristic of a medical image displayed in the medical image 1580 to be imaged may be changed according to the changed parameter value.

Figure 16:
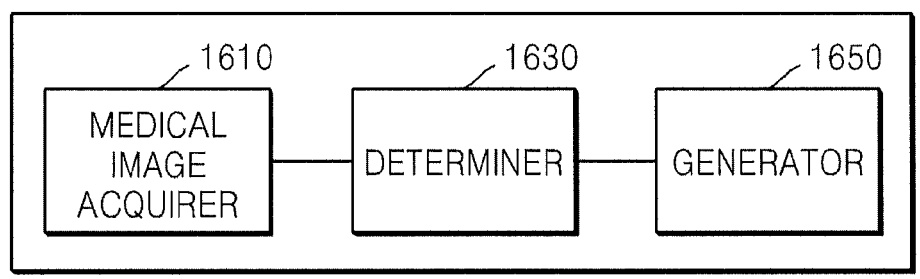
FIG. 16 is a block diagram illustrating a configuration of a medical imaging apparatus according to one or more embodiments.

FIG. 16 is a block diagram illustrating a configuration of a medical imaging apparatus 1600 according to one or more embodiments.

Referring to FIG. 16, the medical imaging apparatus 1600 according to one or more embodiments may include a medical image acquirer 1610, a determiner 1630, and a generator 1650. The medical image acquirer 1610, the determiner 1630, and the generator 1650 may be implemented as a microprocessor.

The medical image acquirer 1610 may acquire the first image of the object 10, which may be imaged according to a predetermined parameter value set in the medical imaging apparatus 1600, and the second medical image changed from the first medical image. The second medical image may include a medical image which is generated by changing the characteristic of the first medical image.

The determiner 1630 may determine a first standard parameter value corresponding to the first medical image and a second standard parameter value corresponding to the second medical image. Specifically, the determiner 1630 may determine the first standard parameter value, corresponding to at least one of the brightness, sharpness, and contrast of the first medical image, from the lookup table, and may determine the second standard parameter value, corresponding to at least one of the brightness, sharpness, and contrast of the second medical image, from the lookup table. Also, the determiner 1630 may determine the first standard parameter value and the second standard parameter value in further consideration of the body information and imaged part of the object 10. Also, when the body information of the object 10 is changed, the determiner 1630 may determine a third standard parameter value corresponding to the changed body information of the object 10.

The generator 1650 may generate a personalized parameter value corresponding to the object 10 on the basis of the first standard parameter value and the second standard parameter value. Also, when the body information of the object 10 is changed, the generator 1650 may update the personalized parameter value on the basis of the third standard parameter value. A method of generating a personalized parameter value and a method of updating a personalized parameter value have been described above, and thus, their detailed descriptions are not provided.

Figure 17:
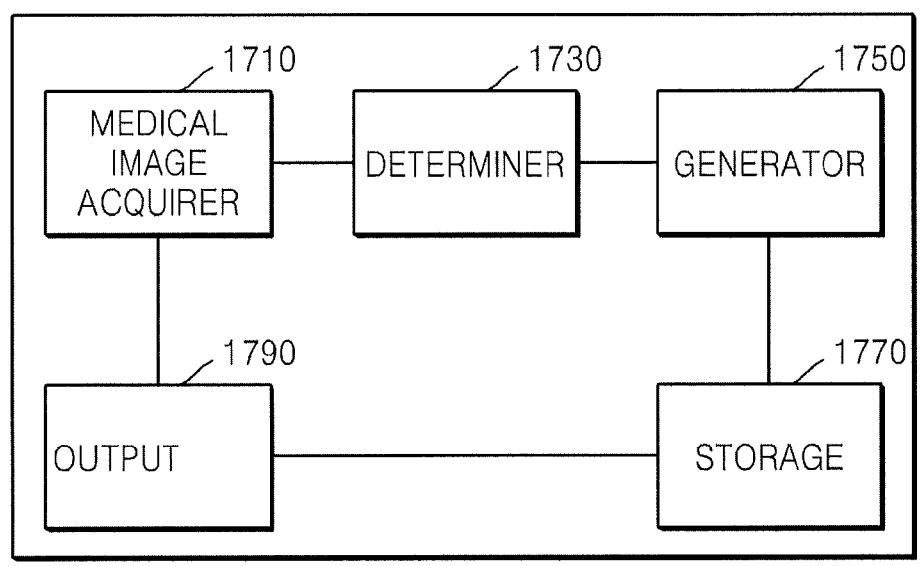
FIG. 17 is a block diagram illustrating a configuration of a medical imaging apparatus according to one or more embodiments.

FIG. 17 is a block diagram illustrating a configuration of a medical imaging apparatus 1700 according to one or more embodiments.

Referring to FIG. 17, the medical imaging apparatus 1700 according to one or more embodiments may include a medical image acquirer 1710, a determiner 1730, a generator 1750, a storage 1770, and an output 1790. The medical image acquirer 1710, the determiner 1730, and the generator 1750 have been described above with reference to FIG. 16, and thus, their detailed descriptions are not provided.

The storage 1770 may store data, and may include a module, enabling information to be inputted/outputted, such as, for example, a hard disk, a flash memory, a compact flash (CF) card, a secure digital (SD) card, a smart media (SM) card, a multimedia card (MMC), or a memory stick, etc.

The storage 1770 may store a lookup table, including a plurality of standard parameter values, and object-imaging information including a personalized parameter value. For example, the storage 1770 may map the personalized parameter value to identification information and body information of an object to store the personalized parameter value, and may map the personalized parameter value to an imaged part of the object to store the personalized parameter value.

A standard parameter value may be previously determined according to body information and an imaged part of a standard object and a characteristic of a standard medical image, and stored as a lookup table. The plurality of standard parameter values included in the lookup table may correspond to respective characteristics of a plurality of standard medical images, and correspond to respective body information and imaged parts of a plurality of standard objects.

The output 1790 may output a personalized parameter value and an updated personalized parameter value which correspond to the object 10. Also, the output 1790 may output object-imaging information including the personalized parameter value.

The output 1790 may include, for example, a speaker, a printer, and a display device such as a CRT device, an LCD device, a PDP, an OLED display device, an FED device, an LED display device, a VFD device, a DLP device, a PFD device, a 3D display device, or a transparent display device, etc. and may include various output devices within a scope obvious to those skilled in the art. Also, the output 1790 may include the display 1500 of FIG. 15.

Figure 18:
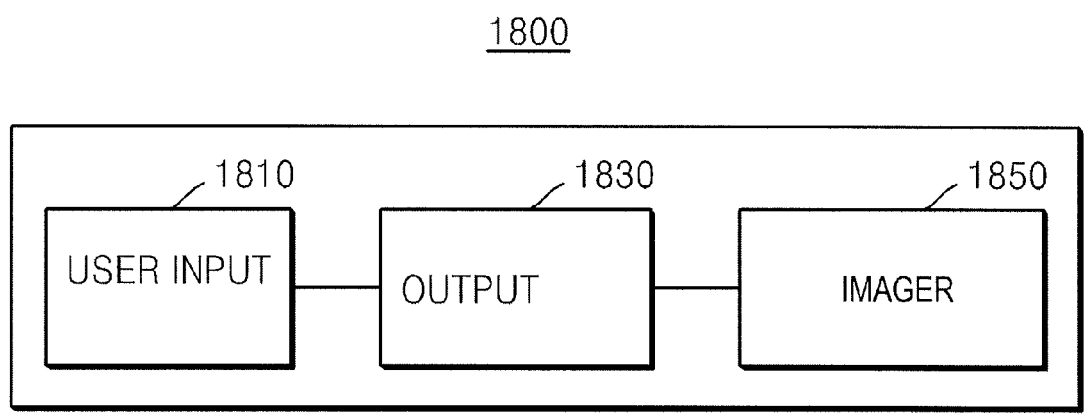
FIG. 18 is a block diagram illustrating a configuration of a medical imaging apparatus according to one or more embodiments.

FIG. 18 is a block diagram illustrating a configuration of a medical imaging apparatus 1800 according to one or more embodiments.

Referring to FIG. 18, the medical imaging apparatus 1800 according to one or more embodiments may include a user input 1810, an output 1830, and an imager 1850.

The user input 1810 may enable a user to input certain data to the medical imaging apparatus 1800, and may include, for example, a keyboard, a mouse, a trackball, a voice recognizer, a gesture recognizer, or a touch screen, etc. Also, the medical imaging apparatus 1800 may include various input devices within a scope obvious to those skilled in the art. The user input 1810 may receive the identification information of the object 10 from the user.

The output 1830 may output a personalized parameter value and an updated personalized parameter value which correspond to the object 10. Also, the output 1830 may output object-imaging information including the personalized parameter value. The output 1830 may include the display 1500 of FIG. 15.

The imager 1850 may receive selection of a personalized parameter value from the user through the user input 1810, and may generate a medical image of the object 10 according to the personalized parameter value. The imager 1850 may include the X-ray generator 110 and detector 130 of FIG. 1.

The medical imaging apparatus 1800 according to one or more embodiments may further include a determiner and a generator.

The determiner may determine a first standard parameter value corresponding to the first medical image and a second standard parameter value corresponding to the second medical image. Specifically, the determiner may determine the first standard parameter value, corresponding to at least one of the brightness, sharpness, and contrast of the first medical image, from the lookup table, and determine the second standard parameter value, corresponding to at least one of the brightness, sharpness, and contrast of the second medical image, from the lookup table. Also, the determiner may determine the first standard parameter value and the second standard parameter value in further consideration of the body information and imaged part of the object 10. Also, when the body information of the object 10 is changed, the determiner may determine a third standard parameter value corresponding to the changed body information of the object 10.

The generator may generate a personalized parameter value corresponding to the object 10 on the basis of the first standard parameter value and the second standard parameter value. Also, when the body information of the object 10 is changed, the generator may update the personalized parameter value on the basis of the third standard parameter value. A method of generating a personalized parameter value and a method of updating a personalized parameter value have been described above, and thus, their detailed descriptions are not provided.

Figure 19:
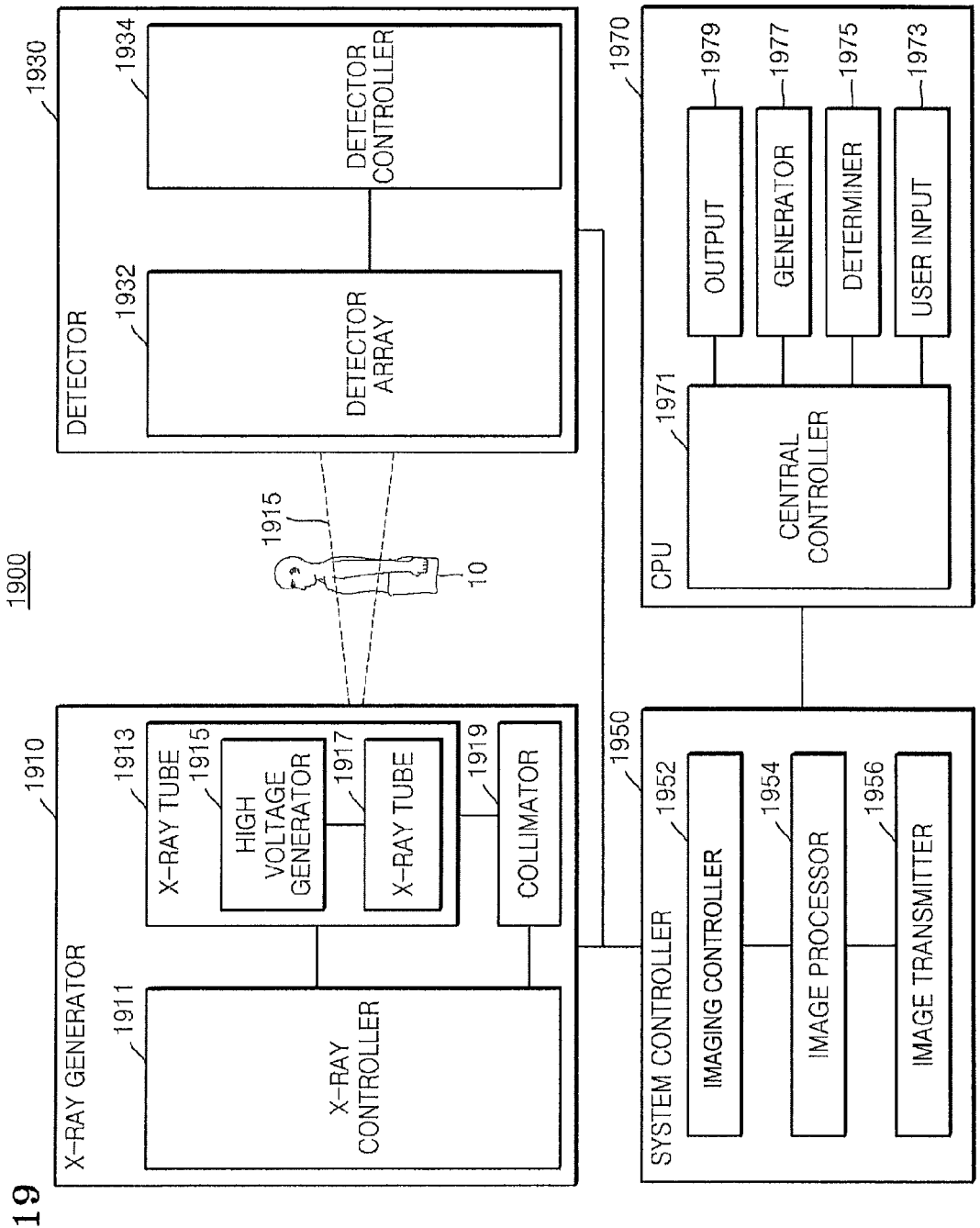
FIG. 19 is a block diagram illustrating a configuration of a medical imaging apparatus according to one or more embodiments.

FIG. 19 is a block diagram illustrating a configuration of a medical imaging apparatus 1900 according to one or more embodiments.

Referring to FIG. 19, the medical imaging apparatus 1900 according to one or more embodiments may include an X-ray generator 1910, a detector 1930, a system controller 1950, and a central processing (CPU) 1970. The medical imaging apparatus 1900 of FIG. 19 may be a fixed-type medical imaging apparatus or a mobile medical imaging apparatus. The X-ray generator 1910 and the detector 1930 may correspond to the imager 1850 of FIG. 18.

The medical imaging apparatus 1900 may further include a communicator that communicates with an external server or other medical apparatuses. The communicator may be included in at least one of the X-ray generator 1910, the detector 1930, the system controller 1950, and the CPU 1970, or may be a separate element that is connected to at least one of the X-ray generator 1910, the detector 1930, the system controller 1950, and the CPU 1970. The communicator will be described below with reference to FIG. 20.

The X-ray generator 1910, the detector 1930, the system controller 1950, and the CPU 1970 may be connected to each other in a wired/wireless manner, and when connected in the wireless manner, the medical imaging apparatus 1900 may further include an element (not shown) for synchronizing clocks therebetween.

The X-ray generator 1910 may irradiate X-rays 1915 on the object 10. The object 10 may be disposed between the X-ray generator 1910 and the detector 1930, may stand, or may lie on a table. Also, the object 10 may be located in a gantry.

The X-ray generator 1910 may include an X-ray tube 1913, a collimator 1919, and an X-ray controller 1911.

The X-ray tube 1913 may include a high voltage generator 1915 that may generate a high-voltage current and an X-ray tube 1917. The X-ray tube 1917 may generate the X-rays 1915 with the high-voltage current generated by the high voltage generator 1915. A wavelength of the X-rays 1915 may be adjusted according to a voltage intensity of the high-voltage current, and an intensity of the X-rays 1915 may be adjusted according to a current intensity of the high-voltage current.

The collimator 1919 may control a direction and width of the X-rays 1915 irradiated on the object 10. The X-rays 1915 may reach a region of interest (ROI) of the object 10 according to an operation of the collimator 1919, and an amount of X-rays irradiated on the object 10 may be reduced.

The X-ray controller 1911 may control the X-ray tube 1913 and the collimator 1919. Specifically, the X-ray controller 1911 may control a position of the X-ray tube 1913 and a position of the collimator 1919, thus enabling the X-rays 1915 to accurately reach the ROI of the object 10. Also, the X-ray controller 1911 may control an X-ray irradiation timing, an X-ray wavelength, and an X-ray intensity according to a imaging condition transferred from the system controller 1950.

The detector 1930 may receive the X-rays 1915 which pass through or by the object 10, and may generate image data corresponding to an intensity of the received X-rays 1915. The X-ray generator 1910 and the detector 1930 may be variously disposed with the object 10 therebetween.

The detector 1930 may include a detector array 1932 and a detector controller 1934. When the detector 1930 of FIG. 19 is a wireless detector, the detector 1930 may further include a battery and a wireless interface. Also, the detector 1930 of FIG. 19 may include a fixed detector or a mobile detector.

The detector array 1932 may convert photons of the X-rays 1915, which pass through or by the object 10 and are received, into light photons having lower energy. The detector array 1932 may convert the light photons into electrical signals corresponding to intensities of the photons, and may convert the electrical signals into digital signals to generate image data. Also, the detector array 1932 may correct gain values of the electrical signals, and may convert the gain value-corrected electrical signals into digital signals.

The detector controller 1934 may control the detector 1930. Specifically, the detector controller 1934 may adjust a position of the detector 1930 according to the imaging condition received from the system controller 1950, and may control an operation timing of the detector array 1932. The detector controller 1934 may transmit the image data, acquired from the detector array 1932, to the system controller 1950. Also, the detector controller 1934 may switch the detector 1930 from a sleep mode to a standby mode, or switch the detector from the standby mode to the sleep mode. The sleep mode may include a state in which the detector array 1932 except the detector controller 1934 is set to be turned off, and the standby mode may include a state in which the detector array 1932 and the detector controller 1934 both remain turned on.

The system controller 1950 may include a imaging controller 1952, an image processor 1954, and an image transmitter 1956.

The imaging controller 1952 may transmit position information, imaging timing information, and a imaging condition of each of the X-ray generator 1910 and the detector 1930 to the X-ray controller 1911 and the detector controller 1934 according to a imaging condition and certain control information received from the CPU 1970.

The image processor 1954 may receive the image data transmitted from the detector controller 1934, and may process the received image data to generate a medical image of the object 10. Specifically, the image processor 1954 may receive the image data from the detector controller 1934, may remove noise from the image data, and may adjust a dynamic range and interleaving to generate the medical image of the object 10. Also, the image processor 1954 may encode the medical image at a predetermined compression rate.

The image transmitter 1956 may transmit the medical image, received from the image processor 1954, to the CPU 1970.

The CPU 1970 may be located in an operating room, unlike the X-ray generator 1910, the detector 1930, and the system controller 1950. The CPU 1970 may receive an imaging condition and certain control information for generating a medical image from a user, and may transmit the imaging condition and the certain control information to the system controller 1950. Also, the CPU 1970 may output the medical image and medical image-related information to the user by using the medical image received from the system controller 1950.

The CPU 1970 may include a central controller 1971, a user input 1973, a determiner 1975, a generator 1977, and an output 1979.

The central controller 1971 may control an operation of the CPU 1970. Specifically, the user controls transmission of an imaging condition (which may be inputted through the user input 1973) to the system controller 1950, or may control an output of the medical image transmitted from the system controller 1950. When the medical image received from the system controller 1950 is encoded, the central controller 1971 may decode the encoded medical image in a decoding method corresponding to an encoding method.

The user input 1973 may receive a certain input from the user. The user input 1973 may include, for example, a keyboard, a mouse, a touch screen, a voice recognizer, a fingerprint recognizer, an iris recognizer, or the like, and may include an input device obvious to those skilled in the art. The user may input an imaging condition and certain control information of a medical image by using the user input 1973. Also, the user input 1973 may receive the identification information of the object 10 from the user.

The determiner 1975 may determine a first standard parameter value corresponding to the first medical image and a second standard parameter value corresponding to the second medical image. Specifically, the determiner 1975 may determine the first standard parameter value, corresponding to, for example, at least one of the brightness, sharpness, and contrast, etc. of the first medical image, from the lookup table, and may determine the second standard parameter value, corresponding to, for example, at least one of the brightness, sharpness, and contrast, etc. of the second medical image, from the lookup table. Also, the determiner 1975 may determine the first standard parameter value and the second standard parameter value in further consideration of the body information and imaged part of the object 10. Also, when the body information of the object 10 is changed, the determiner 1975 may determine a third standard parameter value corresponding to the changed body information of the object 10.

The generator 1977 may generate a personalized parameter value corresponding to the object 10 on the basis of the first standard parameter value and the second standard parameter value. Also, when the body information of the object 10 is changed, the generator 1977 may update the personalized parameter value on the basis of the third standard parameter value. A method of generating a personalized parameter value and a method of updating a personalized parameter value have been described above, and thus, their detailed descriptions are not provided.

The output 1979 may output certain information to the user by using a medical image. Also, the output 1979 may output a personalized parameter value and an updated personalized parameter value which correspond to the object 10. Also, the output 1979 may output object-imaging information including the personalized parameter value. The output 1979 may include the display 1500 of FIG. 15.

The medical imaging apparatus 1900 of FIG. 19 may include a plurality of digital signal processors (DSPs), a microminiature arithmetic operation apparatus, and a special-purpose (for example, fast A/D conversion, fast Fourier transform, array processing, etc.) processing circuit.

Also, in FIG. 19, the X-ray generator 1910, the detector 1930, and the system controller 1950 are illustrated as being separate elements, but it is obvious to those skilled in the art that some of elements included in each of the X-ray generator 1910, the detector 1930, and the system controller 1950 may be included in a different element. For example, the X-ray controller 1911 of the X-ray generator 1910 and the detector controller 1934 of the detector 1930 may be omitted from the X-ray generator and the detector 1930, respectively, and may instead be included in the system controller 1950.

Communication between the X-ray generator 1910 and the system controller 1950 and between the detector 1930 and the system controller 1950 may use a high-speed digital interface such as low voltage differential signalling (LVDS), asynchronous serial communication such as universal asynchronous receiver transmitter (UART), a low delay type network protocol such as synchronous serial communication or a controller area network (CAN), and use various communication methods within a scope obvious to those skilled in the art.

Also, communication between the system controller 1950 and the CPU 1970 may use gigabit Ethernet (registered trademark), and may use various communication methods within a scope obvious to those skilled in the art.

Figure 20:
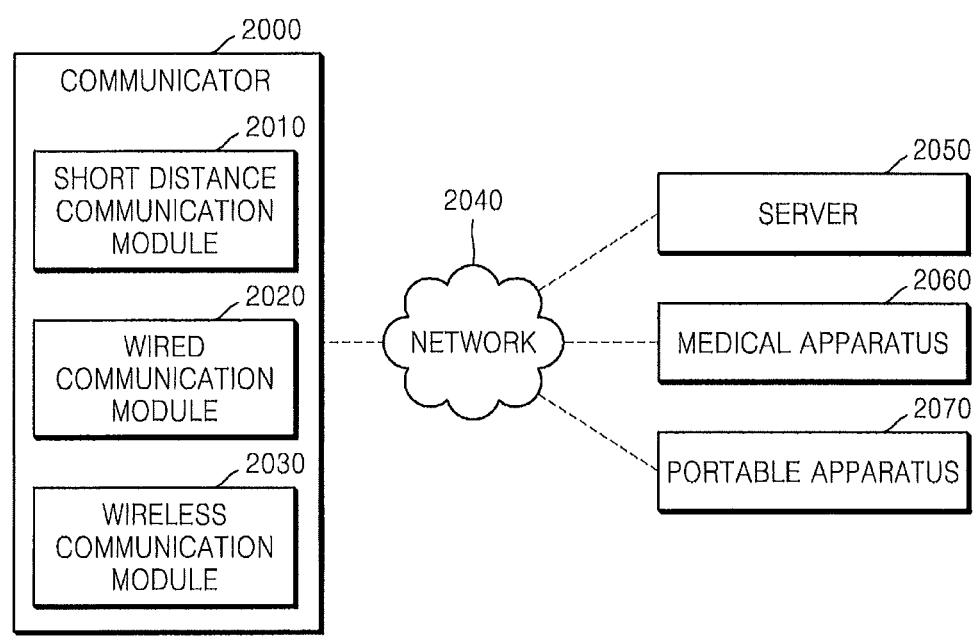
FIG. 20 is a diagram illustrating a configuration of a communicator included in a medical imaging apparatus according to one or more embodiments, such as the medical imaging apparatus of FIG. 19.

FIG. 20 is a diagram illustrating a configuration of a communicator 2000 that may be included in a medical imaging apparatus according to one or more embodiments, such as the medical imaging apparatus 1900 of FIG. 19.

The communicator 2000 may be connected to a network 2040 a wired/wireless manner, and may communicate with an external server 2050, an external medical apparatus 2060, or an external portable apparatus 2070.

The communicator 2000 may transmit and receive data associated with a diagnosis of the object 10 over the network 2040, and may also transmit and receive a medical image generated by the different medical apparatus 2060 such as a CT apparatus, an MRI apparatus, an X-ray apparatus, or the like. Further, the communicator 2000 may receive a diagnosis history or treatment schedule of a patient from the server 2050, and use the received diagnosis history or treatment schedule in diagnosing the object 10. Also, the communicator 2000 may communicate with the portable apparatus 2070 such as a mobile terminal, PDA, notebook computer, or the like of a doctor or a customer, in addition to the server 2050 or medical apparatus 2060 of a hospital.

The communicator 2000 may include one or more elements enabling communication with an external apparatus, and for example, may include a short distance communication module 2010, a wired communication module 2020, and a wireless communication module 2030.

The short distance communication module 2010 may denote a module for performing short-distance communication with an apparatus within a certain distance. Short-distance communication technology according to one or more embodiments may include, for example, wireless LAN, Wi-Fi, Bluetooth, zigbee, Wi-Fi direct (WFD), ultra wideband (UWB), infrared data association (IrDA), Bluetooth low energy (BLE), and near field communication (NFC), or the like, but is not limited thereto.

The wired communication module 2020 may denote a module for performing communication using an electrical signal or an optical signal. Wired communication technology may include wired communication technology using, for example, a pair cable, a coaxial cable, and an optical fiber cable, etc. and may include wired communication technology obvious to those skilled in the art.

The wireless communication module 2030 may transmit and receive a radio frequency (RF) signal to and from at least one of, for example, a base station, an external apparatus, and a server over a mobile network. Here, the RF signal may include various types of data based on transmission and reception of, for example, a voice call signal, a video call signal, or a letter/multimedia message.

In one or more embodiments, any apparatus, system, element, or interpretable unit descriptions herein include one or more hardware devices or hardware processing elements. For example, in one or more embodiments, any described apparatus, system, element, retriever, pre or post-processing elements, tracker, detector, encoder, decoder, etc., may further include one or more memories and/or processing elements, and any hardware input/output transmission devices, or represent operating portions/aspects of one or more respective processing elements or devices. Further, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include: magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be any defined, measurable, and tangible distributed network, so that the computer readable code is stored and executed in a distributed fashion. Still further, as only an example, the processing element could include a processor or a computer processor, and processing elements may be distributed and/or included in a single device.

The computer-readable media may also be embodied in at least one application specific integrated circuit (ASIC) or Field Programmable Gate Array (FPGA), as only examples, which execute (e.g., processes like a processor) program instructions.

While aspects of the present invention have been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A method of generating a personalized parameter value for generating a medical image, the method comprising:
   determining, using a computer, a first standard parameter value corresponding to a first medical image containing an object imaged according to a predetermined parameter value and a second standard parameter value corresponding to a second medical image where the second medical image is a post-corrected image of the first medical image;
   generating, using the computer, a personalized parameter value on a basis of the first standard parameter value and the second standard parameter value where the personalized parameter value is optimized for the object using one of a ratio and a difference between the first and second standard parameters; and
   generating, using the computer, a visible image containing the object where the personalized parameter value is optimized for the object,
   wherein the visible image is a visible image produced by X-ray radiation.

2. The method of claim 1, wherein the second medical image comprises a medical image which is generated by changing an image characteristic of the first medical image.

3. The method of claim 2, wherein the determining of the first standard parameter value and the second standard parameter value comprises determining the first standard parameter value corresponding to the first medical image and the second standard parameter value corresponding to the second medical image from a lookup table.

4. The method of claim 3, wherein the determining of the first standard parameter value and the second standard parameter value comprises determining the first standard parameter value and the second standard parameter value in correspondence with body information and an imaged part of the object.

5. The method of claim 3, wherein the lookup table comprises a plurality of standard parameter values, the plurality of standard parameter values respectively corresponding to body information and imaged part of each of a plurality of standard objects.

6. The method of claim 3, wherein the lookup table comprises a plurality of standard parameter values, the plurality of standard parameter values respectively corresponding to image characteristic of each of a plurality of medical images.

7. The method of claim 1, wherein when the second medical image is a medical image generated by changing a contrast of the first medical image, and there is no second standard parameter value corresponding to a contrast of the second medical image, the determining of the second standard parameter value comprises using the contrast of the first medical image as the contrast of the second medical image to determine the second standard parameter value corresponding to the second medical image.

8. The method of claim 7, wherein the determining of a second standard parameter value comprises:
   determining a second pixel value region on a histogram of the electronic medical image, wherein the second pixel value region has a total number of pixel values which is less than a total number of pixel values in a first pixel value region on a histogram of the first medical image; and
   determining the second standard parameter value corresponding to a brightness of the second medical image of when pixels included in the first pixel value region are moved to the second pixel value region.

9. The method of claim 8, wherein the determining of the second standard parameter value comprises:
   determining a third pixel value region on the histogram of the second medical image, wherein the third pixel value region comprises pixel values corresponding to a number of pixels that is changed from a number of pixels corresponding to pixel values of the histogram of the first medical image; and
   determining, as the second pixel value region, a region from a start point of the third pixel value region to a point separated therefrom by a distance of the first pixel value region.

10. The method of claim 1, wherein the generating of a personalized parameter value comprises changing the predetermined parameter value according to a relationship between the first standard parameter value and the second standard parameter value to generate the personalized parameter value.

11. The method of claim 1, wherein the generating of a personalized parameter value comprises changing the second standard parameter value according to a relationship between the first standard parameter value and the predetermined parameter value to generate the personalized parameter value.

12. The method of claim 1, further comprising:

when body information of the object is changed after the personalized parameter value is generated, determining a third standard parameter value, corresponding to an image characteristic of the second medical image and the changed body information of the object, from a lookup table; and updating the personalized parameter value on a basis of the third standard parameter value.

13. A medical imaging apparatus comprising:

a computer configured to:
- determine, using the computer, a first standard parameter value corresponding to a first medical image of an object imaged according to a predetermined parameter value and a second standard parameter value corresponding to a second medical image where the second medical image is a post-corrected image of the first medical image;
- generate, using the computer, a personalized parameter value corresponding to the object on a basis of the first standard parameter value and the second standard parameter value where the personalized parameter value is optimized for the object using one of a ratio and a difference between the first and second standard parameters;
- capture a personalized object medical X-ray image of the object using the personalized parameter value; and
- generate, using the computer, a visible image containing the object where the personalized parameter value is optimized for the object,
- wherein the visible image is a visible image produced from the X-ray image.

14. The apparatus of claim 13, wherein the second medical image medical image comprises a medical image which is generated by changing an image characteristic of the first medical image.

15. The apparatus of claim 14, wherein the determiner determines the first standard parameter value corresponding to the first medical image and the second standard parameter value corresponding to the second medical image from a lookup table.

16. A medical imaging method of generating a medical image of an object, the medical imaging method comprising:

receiving identification information of the object from a user;

outputting a personalized parameter value corresponding to the identification information of the object using a first standard parameter value corresponding to a first medical image containing an object imaged according to a predetermined parameter value and a second standard parameter value corresponding to a second medical image where the second medical image is a post-corrected image of the first medical image where the personalized parameter value is generated using one of a ratio and a difference between the first and second standard parameters;

receiving a selection of the personalized parameter value from the user; and generating, using a computer, the medical image of the object according to the personalized parameter value selected by the user where the personalized parameter value is optimized for the object; and generating, using the computer, a visible image containing the object where the personalized parameter value is optimized for the object wherein the visible image is a visible image produced by X-ray radiation.

17. The medical imaging method of claim 16, wherein the outputting of a personalized parameter value comprises displaying a second medical image changed from a pre-imaged first medical image of the object according to a predetermined parameter value set in a medical imaging apparatus, and the personalized parameter value.

18. The medical imaging method of claim 17, wherein the displaying comprises displaying an adjustment window for adjusting the personalized parameter value.

19. The medical imaging method of claim 18, wherein when the user changes the personalized parameter value by using the adjustment window, the displaying comprising changing the second medical image according to the changed personalized parameter value, and displaying the changed second medical image as a medical image to be generated.

20. The medical imaging method of claim 16, further comprising:

determining a first standard parameter value which corresponds to a pre-imaged first medical image of the object according to a predetermined parameter value set in a medical imaging apparatus and a second standard parameter value which corresponds to a second medical image changed from the pre-imaged first medical image; and generating the personalized parameter value on a basis of the first standard parameter value and the second standard parameter value where the personalized parameter value is optimized for the object.

* * * * *